United States Patent
Dong

(10) Patent No.: US 7,410,948 B2
(45) Date of Patent: *Aug. 12, 2008

(54) ANALOGS OF PARATHYROID HORMONE

(75) Inventor: Zheng Xin Dong, Holliston, MA (US)

(73) Assignee: Societe de Conseils de Recherches Et d'Applications Scientifiques, SAS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/684,383

(22) Filed: Mar. 9, 2007

(65) Prior Publication Data

US 2007/0299009 A1    Dec. 27, 2007

Related U.S. Application Data

(60) Continuation of application No. 11/094,662, filed on Mar. 30, 2005, which is a division of application No. 10/289,519, filed on Nov. 6, 2002, now Pat. No. 6,921, 750, which is a continuation of application No. 09/399, 499, filed on Sep. 20, 1999, now Pat. No. 6,544,949, which is a continuation-in-part of application No. 08/779,768, filed on Jan. 7, 1997, now Pat. No. 5,969, 095, and a continuation-in-part of application No. 09/341,217, filed as application No. PCT/US97/22498 on Dec. 8, 1997, now abandoned, which is a continuation-in-part of application No. 08/813,534, filed on Mar. 7, 1997, now Pat. No. 5,955,574, which is a continuation-in-part of application No. 08/779,768, filed on Jan. 7, 1997, now Pat. No. 5,969,095, which is a continuation-in-part of application No. 08/626,186, filed on Mar. 29, 1996, now Pat. No. 5,723,577.

(60) Provisional application No. 60/003,305, filed on Sep. 6, 1995, provisional application No. 60/001,105, filed on Jul. 13, 1995.

(51) Int. Cl.
*A61K 38/29* (2006.01)
*C07K 14/635* (2006.01)

(52) U.S. Cl. .................................. 514/12; 530/324

(58) Field of Classification Search .................. None
See application file for complete search history.

(56) References Cited

U.S. PATENT DOCUMENTS

| | | |
|---|---|---|
| 4,656,250 A | 4/1987 | Morita et al. |
| 5,434,246 A | 7/1995 | Fukuda et al. |
| 5,455,329 A | 10/1995 | Wingender et al. |
| 5,457,047 A | 10/1995 | Wingender et al. |
| 5,589,452 A | 12/1996 | Krstenansky et al. |
| 5,599,792 A | 2/1997 | Kronis et al. |
| 5,723,577 A | 3/1998 | Dong |
| 5,955,574 A | 9/1999 | Dong |
| 5,969,095 A | 10/1999 | Dong |
| 6,544,949 B1 | 4/2003 | Dong |
| 6,921,750 B2 * | 7/2005 | Dong .................... 514/12 |

FOREIGN PATENT DOCUMENTS

| | | |
|---|---|---|
| AU | 64834/96 | 7/1999 |
| EP | 0 293 1 5 8 | 11/1988 |
| EP | 451867 | 10/1991 |
| EP | 0 561 412 | 9/1993 |
| EP | 0 672 057 | 9/1995 |
| EP | 748817 | 12/1996 |
| EP | 0 477 885 | 1/1999 |
| GB | 2269176 | 2/1994 |
| HU | P9500110 | 6/1995 |
| HU | P9500115 | 6/1995 |
| HU | 217 843 B | 9/1995 |
| JP | 6-184198 | 7/1994 |
| WO | WO 90/10067 | 9/1990 |
| WO | WO 93/06846 | 4/1993 |
| WO | WO 94/01460 | 1/1994 |
| WO | WO 94/02510 | 2/1994 |
| WO | WO 95/02610 | 1/1995 |
| WO | 95/04752 | 2/1995 |
| WO | WO 96/19246 | 6/1996 |
| WO | WO 96/40775 | 12/1996 |
| WO | WO 97/02834 | 1/1997 |

OTHER PUBLICATIONS

Gardella, T.J. et al.; "Parathyroid Hormone (PTH)-PTH-Related Peptide Hybrid Peptides Reveal Functional Interactions Between The 1-14 and 15-34 Domains of the Ligand"; J. Biol. Chem., vol. 270, No. 12, pp. 6584-6588, (1995).

Barden et al.,; "NMR Solution Structure of Human Parathyroid Hormone (1-34)"; Biochemistry 32:7126-7132; (1993).

Cohen et al.; "Analogues of Parathyroid Hormone Modified at Positions at 6"; The Journal of Biological Chemistry 266:No. 3; 1997-2004; (1991).

Karle et al.; "Structural Characteristics of a-Helical Peptide Molecules Containing Aib Residues"; Biochemistry 29:No. 29;6747-6756; (1990).

Leaffer et al.; Modulation of Osteogenic Cell Ultrastructure by RS-23581; an Analog of Human Parathyroid Hormone (PTH)-Related Peptide-(1-34), and Bovine PTH-(1-34); Endocrinology 136:No. 8;3624-3631, (1995).

Li et al.; "A Measure of Helical Propensity for Amino Acids in Membrane Environments"; Structural Biology 1:No. 6;368-373; (1994).

McLean et al.; "Minimal Peptide Length for Interaction of Amphipathic a-Helical Peptides with Phosphatidylcholine Liposomes"; Biochemistry 30-:31-37; (1991).

Neugebauer et al.; "Structural Elements of Human Parathyroid Hormone and Their Possible Relation to Biological Activites"; Biochemistry 31:2056-2063; (' 1992).

(Continued)

*Primary Examiner*—Jeffrey E Russel
(74) *Attorney, Agent, or Firm*—Fish & Richardson; Alan F. Feeney; Tony K. Uhm

(57) ABSTRACT

The present invention is directed to peptide analogues of fragment of parathyroid hormone (PTH) or parathyroid hormone-related protein (PTHrP), a method of using said analogues alone or in combination with a bisphosphonate or calcitonin to treat osteoporosis and pharmaceutical compositions comprising said analogues alone or in combination with a bisphosphonate or calcitonin.

2 Claims, No Drawings

OTHER PUBLICATIONS

Strickland et al.; "Structure of Human Parathyroid Hormone (1-34) in the Presence of Solvents and Micelles"; Biochemistry 32:6050-6057; (1993).

Surewicz et al.; "Structure-function Relationships in Human Parathyroid Hormone: The Essential Role of Amphiphilic a-Helix"; Peptide Hormones Hormone: The Essential Role of Amphiphilic a-Helix; Peptide Hormones 556-558, not dated.

Lynn H. Caporale et al.; "Characterization of parathyroid hormone antagonists" Peptides, Chemistry and Biology; Proceedings of the Tenth American Peptide Symposium; (1987): pp. 449-451.

Horiuchi N. et al.; "Similarity of synthetic peptide from human tumor to parathyroid hormone in vivo and in vitro" Science; (1987); vol. 238, pp. 1566-1568.

Chorev et al., "Modifications of Position 12 in Parathyroid Hormone . . . ", 1990, Biochem., vol. 29(6);1580-1586.

* cited by examiner

SEQUENCE LISTING

<160> NUMBER OF SEQ ID NOS: 5

<210> SEQ ID NO 1
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser, Ala, or Dap
<220> FEATURE:
<221> NAME/KEY: VARIANT
<222> LOCATION: 3
<223> OTHER INFORMATION: Xaa = Ser, Thr, or Aib
<220> FEATURE:
<221> NAME/KEY: VARIANT
<222> LOCATION: 5
<223> OTHER INFORMATION: Xaa = Leu, Nle, Ile, Cha, beta-Nal, Trp, Pal,
     Acc, Phe or p-X-Phe in which X is OH, a halogen, or CH3
<220> FEATURE:
<221> NAME/KEY: VARIANT
<222> LOCATION: 7
<223> OTHER INFORMATION: Xaa = Leu, Nle, Ile, Cha, beta-Nal, Trp, Pal,
     Acc, Phe, or p-X-Phe, in which X is OH, a halogen, or CH3
<220> FEATURE:
<221> NAME/KEY: VARIANT
<222> LOCATION: 8
<223> OTHER INFORMATION: Xaa = Met, Nva, Leu, Val, Ile, Cha, Acc, or Nle
<220> FEATURE:
<221> NAME/KEY: VARIANT
<222> LOCATION: 11
<223> OTHER INFORMATION: Xaa = Leu, Nle, Ile, Cha, beta-Nal, Trp, Pal,
     Acc, Phe or p-X-Phe, in which X is OH, a halogen, or CH3
<220> FEATURE:
<221> NAME/KEY: VARIANT
<222> LOCATION: 12
<223> OTHER INFORMATION: Xaa = Gly, Acc, or Aib
<220> FEATURE:
<221> NAME/KEY: VARIANT
<222> LOCATION: 15
<223> OTHER INFORMATION: Xaa = Leu, Nle, Ile, Cha, beta-Nal, Trp, Pal,
     Acc, Phe, or p-X-Phe, in which X is OH, a halogen, or CH3
<220> FEATURE:
<221> NAME/KEY: VARIANT
<222> LOCATION: 16
<223> OTHER INFORMATION: Xaa = Ser, Asn, Ala, or Aib
<220> FEATURE:
<221> NAME/KEY: VARIANT
<222> LOCATION: 17
<223> OTHER INFORMATION: Xaa = Ser, Thr, or Aib
<220> FEATURE:
<221> NAME/KEY: VARIANT
<222> LOCATION: 18
<223> OTHER INFORMATION: Xaa = Met, Nva, Leu, Val, Ile, Nle, Acc, Cha,
     or Aib
<220> FEATURE:
<221> NAME/KEY: VARIANT
<222> LOCATION: 19
<223> OTHER INFORMATION: Xaa = Glu or Aib
<220> FEATURE:
<221> NAME/KEY: VARIANT
<222> LOCATION: 21
<223> OTHER INFORMATION: Xaa = Val, Acc, Cha, or Met
<220> FEATURE:
<221> NAME/KEY: VARIANT
<222> LOCATION: 22
<223> OTHER INFORMATION: Xaa = Acc or Glu
<220> FEATURE:
<221> NAME/KEY: VARIANT
<222> LOCATION: 23
<223> OTHER INFORMATION: Xaa = Trp, Acc, or Cha
<220> FEATURE:
<221> NAME/KEY: VARIANT
<222> LOCATION: 24

```
<223> OTHER INFORMATION: Xaa = Leu, Acc, or Cha
<220> FEATURE:
<221> NAME/KEY: VARIANT
<222> LOCATION: 27
<223> OTHER INFORMATION: Xaa = Lys, Aib, Leu, hArg, Gln, Acc, or Cha
<220> FEATURE:
<221> NAME/KEY: VARIANT
<222> LOCATION: 28
<223> OTHER INFORMATION: Xaa = Leu, Acc, or Cha
<220> FEATURE:
<221> NAME/KEY: VARIANT
<222> LOCATION: 29
<223> OTHER INFORMATION: Xaa = Glu, Acc, or Aib
<220> FEATURE:
<221> NAME/KEY: VARIANT
<222> LOCATION: 30
<223> OTHER INFORMATION: Xaa = Asp or Lys
<220> FEATURE:
<221> NAME/KEY: VARIANT
<222> LOCATION: 31
<223> OTHER INFORMATION: Xaa = Val, Leu, Nle, Acc, Cha, or deleted
<220> FEATURE:
<221> NAME/KEY: VARIANT
<222> LOCATION: 32
<223> OTHER INFORMATION: Xaa = His or deleted
<220> FEATURE:
<221> NAME/KEY: VARIANT
<222> LOCATION: 33
<223> OTHER INFORMATION: Xaa = Asn or deleted
<220> FEATURE:
<221> NAME/KEY: VARIANT
<222> LOCATION: 34
<223> OTHER INFORMATION: Xaa = Phe, Tyr, Amp, Aib, or deleted
<220> FEATURE:
<223> OTHER INFORMATION: This sequence may also encompass a deletion
      peptide with a length of 30, 31, 32 or 33 amino acids

<400> SEQUENCE: 1

Xaa Val Xaa Glu Xaa Gln Xaa Xaa His Asn Xaa Xaa Lys His Xaa Xaa
 1               5                  10                  15

Xaa Xaa Xaa Arg Xaa Xaa Xaa Xaa Arg Lys Xaa Xaa Xaa Xaa Xaa Xaa
            20                  25                  30

Xaa Xaa

<210> SEQ ID NO 2
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser, Ala, or Dap
<220> FEATURE:
<221> NAME/KEY: VARIANT
<222> LOCATION: 3
<223> OTHER INFORMATION: Xaa = Ser, Thr, or Aib
<220> FEATURE:
<221> NAME/KEY: VARIANT
<222> LOCATION: 5
<223> OTHER INFORMATION: Xaa = Leu, Nle, Ile, Cha, beta-Nal, Trp, Pal,
      Phe, or p-X-Phe in which X is OH, a halogen, or CH3
<220> FEATURE:
<221> NAME/KEY: VARIANT
<222> LOCATION: 7
<223> OTHER INFORMATION: Xaa = Leu, Nle, Ile, Cha, beta-Nal, Trp, Pal,
      Phe, or p-X-Phe in which X is OH, a halogen, or CH3
<220> FEATURE:
<221> NAME/KEY: VARIANT
<222> LOCATION: 8
<223> OTHER INFORMATION: Xaa = Met, Nva, Leu, Val, Ile, Cha, or Nle
<220> FEATURE:
<221> NAME/KEY: VARIANT
<222> LOCATION: 11
```

```
<223> OTHER INFORMATION: Xaa = Leu, Nle, Ile, Cha, beta-Nal, Trp, Pal,
      Phe, or p-X-Phe in which X is OH, a halogen, or CH3
<220> FEATURE:
<221> NAME/KEY: VARIANT
<222> LOCATION: 12
<223> OTHER INFORMATION: Gly or Aib
<220> FEATURE:
<221> NAME/KEY: VARIANT
<222> LOCATION: 15
<223> OTHER INFORMATION: Xaa = Leu, Nle, Ile, Cha, beta-Nal, Trp, Pal,
      Phe, or p-X-Phe in which X is OH, a halogen, or CH3
<220> FEATURE:
<221> NAME/KEY: VARIANT
<222> LOCATION: 16
<223> OTHER INFORMATION: Xaa = Ser, Asn, Ala, or Aib
<220> FEATURE:
<221> NAME/KEY: VARIANT
<222> LOCATION: 17
<223> OTHER INFORMATION: Xaa = Ser, Thr, or Aib
<220> FEATURE:
<221> NAME/KEY: VARIANT
<222> LOCATION: (18)
<223> OTHER INFORMATION: Xaa = Met, Nva, Leu, Val, Ile, Nle, Cha, or Aib
<220> FEATURE:
<221> NAME/KEY: VARIANT
<222> LOCATION: 19
<223> OTHER INFORMATION: Xaa = Glu or Aib
<220> FEATURE:
<221> NAME/KEY: VARIANT
<222> LOCATION: 21
<223> OTHER INFORMATION: Xaa = Val, Cha, or Met
<220> FEATURE:
<221> NAME/KEY: VARIANT
<222> LOCATION: 23
<223> OTHER INFORMATION: Xaa = Trp or Cha
<220> FEATURE:
<221> NAME/KEY: VARIANT
<222> LOCATION: 24
<223> OTHER INFORMATION: Xaa = Leu or Cha
<220> FEATURE:
<221> NAME/KEY: VARIANT
<222> LOCATION: 27
<223> OTHER INFORMATION: Xaa = Lys, Aib, Leu, hArg, Gln, or Cha
<220> FEATURE:
<221> NAME/KEY: VARIANT
<222> LOCATION: 28
<223> OTHER INFORMATION: Xaa = Leu or Cha
<220> FEATURE:
<221> NAME/KEY: VARIANT
<222> LOCATION: 30
<223> OTHER INFORMATION: Xaa = Asp or Lys
<220> FEATURE:
<221> NAME/KEY: VARIANT
<222> LOCATION: 31
<223> OTHER INFORMATION: Xaa = Val, Nle, Cha, or deleted
<220> FEATURE:
<221> NAME/KEY: VARIANT
<222> LOCATION: 32
<223> OTHER INFORMATION: Xaa = His or deleted
<220> FEATURE:
<221> NAME/KEY: VARIANT
<222> LOCATION: 33
<223> OTHER INFORMATION: Xaa = Asn or deleted
<220> FEATURE:
<221> NAME/KEY: VARIANT
<222> LOCATION: 34
<223> OTHER INFORMATION: Xaa = Phe, Tyr, Amp, Aib, or deleted
<220> FEATURE:
<223> OTHER INFORMATION: This sequence may also encompass a deletion
      peptide with a length of 30, 31, 32 or 33 amino acids

<400> SEQUENCE: 2

Xaa Val Xaa Glu Xaa Gln Xaa Xaa His Asn Xaa Xaa Lys His Xaa Xaa
 1               5                  10                  15

Xaa Xaa Xaa Arg Xaa Glu Xaa Xaa Arg Lys Xaa Xaa Gln Xaa Xaa Xaa
            20                  25                  30
```

Xaa Xaa

```
<210> SEQ ID NO 3
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Ser, or Dap
<220> FEATURE:
<221> NAME/KEY: VARIANT
<222> LOCATION: 3
<223> OTHER INFORMATION: Xaa = Ser or Aib
<220> FEATURE:
<221> NAME/KEY: VARIANT
<222> LOCATION: 5
<223> OTHER INFORMATION: Xaa = His, Ile, or Cha
<220> FEATURE:
<221> NAME/KEY: VARIANT
<222> LOCATION: 7
<223> OTHER INFORMATION: Xaa = Leu, Cha, Ile, beta-Nal, Trp, Pal, Phe,
     or p-X-Phe in which X is OH, a halogen, or CH3
<220> FEATURE:
<221> NAME/KEY: VARIANT
<222> LOCATION: 8
<223> OTHER INFORMATION: Xaa = Leu, Met or Cha
<220> FEATURE:
<221> NAME/KEY: VARIANT
<222> LOCATION: 10
<223> OTHER INFORMATION: Xaa = Asp or Asn
<220> FEATURE:
<221> NAME/KEY: VARIANT
<222> LOCATION: 11
<223> OTHER INFORMATION: Xaa = Lys, Leu, Cha, Phe, or beta-Nal
<220> FEATURE:
<221> NAME/KEY: VARIANT
<222> LOCATION: 12
<223> OTHER INFORMATION: Xaa = Gly or Aib
<220> FEATURE:
<221> NAME/KEY: VARIANT
<222> LOCATION: 14
<223> OTHER INFORMATION: Xaa = Ser or His
<220> FEATURE:
<221> NAME/KEY: VARIANT
<222> LOCATION: 15
<223> OTHER INFORMATION: Xaa = Ile or Cha
<220> FEATURE:
<221> NAME/KEY: VARIANT
<222> LOCATION: 16
<223> OTHER INFORMATION: Xaa = Gln or Aib
<220> FEATURE:
<221> NAME/KEY: VARIANT
<222> LOCATION: 17
<223> OTHER INFORMATION: Xaa = Asp or Aib
<220> FEATURE:
<221> NAME/KEY: VARIANT
<222> LOCATION: 18
<223> OTHER INFORMATION: Xaa = Leu, Aib, or Cha
<220> FEATURE:
<221> NAME/KEY: VARIANT
<222> LOCATION: 19
<223> OTHER INFORMATION: Xaa = Arg or Aib
<220> FEATURE:
<221> NAME/KEY: VARIANT
<222> LOCATION: 22
<223> OTHER INFORMATION: Xaa = Phe, Glu, Aib, or Cha
<220> FEATURE:
<221> NAME/KEY: VARIANT
<222> LOCATION: 23
<223> OTHER INFORMATION: Xaa = Phe, Leu, Lys, or Cha
<220> FEATURE:
<221> NAME/KEY: VARIANT
<222> LOCATION: 24
<223> OTHER INFORMATION: Xaa = Leu, Lys, or Cha
<220> FEATURE:
```

```
<221> NAME/KEY: VARIANT
<222> LOCATION: 25
<223> OTHER INFORMATION: Xaa = His, Aib, or Glu
<220> FEATURE:
<221> NAME/KEY: VARIANT
<222> LOCATION: 26
<223> OTHER INFORMATION: Xaa = His, Aib, or Lys
<220> FEATURE:
<221> NAME/KEY: VARIANT
<222> LOCATION: 27
<223> OTHER INFORMATION: Xaa = Leu, Lys, or Cha
<220> FEATURE:
<221> NAME/KEY: VARIANT
<222> LOCATION: 28
<223> OTHER INFORMATION: Xaa = Ile, Leu, Lys, or Cha
<220> FEATURE:
<221> NAME/KEY: VARIANT
<222> LOCATION: 29
<223> OTHER INFORMATION: Xaa = Ala, Glu, or Aib
<220> FEATURE:
<221> NAME/KEY: VARIANT
<222> LOCATION: 30
<223> OTHER INFORMATION: Xaa = Glu, Cha, Aib, or Lys
<220> FEATURE:
<221> NAME/KEY: VARIANT
<222> LOCATION: 31
<223> OTHER INFORMATION: Xaa = Ile, Leu, Cha, Lys, or deleted
<220> FEATURE:
<221> NAME/KEY: VARIANT
<222> LOCATION: 32
<223> OTHER INFORMATION: Xaa = His or deleted
<220> FEATURE:
<221> NAME/KEY: VARIANT
<222> LOCATION: 33
<223> OTHER INFORMATION: Xaa = Thr or deleted
<220> FEATURE:
<221> NAME/KEY: VARIANT
<222> LOCATION: 34
<223> OTHER INFORMATION: Xaa = Ala or deleted
<220> FEATURE:
<223> OTHER INFORMATION: This sequence may also encompass a deletion
      peptide with a length of 30, 31, 32 or 33 amino acids

<400> SEQUENCE: 3

Xaa Val Xaa Glu Xaa Gln Xaa Xaa His Xaa Xaa Xaa Lys Xaa Xaa Xaa
  1               5                  10                  15

Xaa Xaa Xaa Arg Arg Xaa Xaa Xaa Xaa Xaa Xaa Xaa Xaa Xaa Xaa Xaa
             20                  25                  30

Xaa Xaa

<210> SEQ ID NO 4
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Ser, or Dap
<220> FEATURE:
<221> NAME/KEY: VARIANT
<222> LOCATION: 3
<223> OTHER INFORMATION: Xaa = Ser or Aib
<220> FEATURE:
<221> NAME/KEY: VARIANT
<222> LOCATION: 5
<223> OTHER INFORMATION: Xaa = His, Ile, or Cha
<220> FEATURE:
<221> NAME/KEY: VARIANT
<222> LOCATION: 7
<223> OTHER INFORMATION: Leu, Cha, Ile, beta-Nal, Trp, Pal, Phe, or
      p-X-Phe in which X is OH, a halogen, or CH3
<220> FEATURE:
<221> NAME/KEY: VARIANT
```

```
<222> LOCATION: 8
<223> OTHER INFORMATION: Xaa = Leu, Met, or Cha
<220> FEATURE:
<221> NAME/KEY: VARIANT
<222> LOCATION: 10
<223> OTHER INFORMATION: Xaa = Asp or Asn
<220> FEATURE:
<221> NAME/KEY: VARIANT
<222> LOCATION: 11
<223> OTHER INFORMATION: Xaa = Lys, Leu, Cha, Phe, or beta-Nal
<220> FEATURE:
<221> NAME/KEY: VARIANT
<222> LOCATION: 12
<223> OTHER INFORMATION: Xaa = Gly or Aib
<220> FEATURE:
<221> NAME/KEY: VARIANT
<222> LOCATION: 14
<223> OTHER INFORMATION: Xaa = Ser or His
<220> FEATURE:
<221> NAME/KEY: VARIANT
<222> LOCATION: 15
<223> OTHER INFORMATION: Xaa = Ile or Cha
<220> FEATURE:
<221> NAME/KEY: VARIANT
<222> LOCATION: 16
<223> OTHER INFORMATION: Xaa = Gln or Aib
<220> FEATURE:
<221> NAME/KEY: VARIANT
<222> LOCATION: 17
<223> OTHER INFORMATION: Xaa = Asp or Aib
<220> FEATURE:
<221> NAME/KEY: VARIANT
<222> LOCATION: 18
<223> OTHER INFORMATION: Xaa = Leu, Aib or Cha
<220> FEATURE:
<221> NAME/KEY: VARIANT
<222> LOCATION: 19
<223> OTHER INFORMATION: Xaa = Arg or Aib
<220> FEATURE:
<221> NAME/KEY: VARIANT
<222> LOCATION: 22
<223> OTHER INFORMATION: Xaa = Phe, Glu, Aib, Acc, or Cha
<220> FEATURE:
<221> NAME/KEY: VARIANT
<222> LOCATION: 23
<223> OTHER INFORMATION: Xaa = Phe, Leu, Lys, Acc, or Cha
<220> FEATURE:
<221> NAME/KEY: VARIANT
<222> LOCATION: 24
<223> OTHER INFORMATION: Xaa = Leu, Lys, Acc, or Cha
<220> FEATURE:
<221> NAME/KEY: VARIANT
<222> LOCATION: 25
<223> OTHER INFORMATION: Xaa = His, Aib, or Glu
<220> FEATURE:
<221> NAME/KEY: VARIANT
<222> LOCATION: 26
<223> OTHER INFORMATION: Xaa = His, Aib, or Lys
<220> FEATURE:
<221> NAME/KEY: VARIANT
<222> LOCATION: 27
<223> OTHER INFORMATION: Xaa = Leu, Lys, Acc, or Cha
<220> FEATURE:
<221> NAME/KEY: VARIANT
<222> LOCATION: 28
<223> OTHER INFORMATION: Xaa = Ile, Leu, Lys, Acc, or Cha
<220> FEATURE:
<221> NAME/KEY: VARIANT
<222> LOCATION: 29
<223> OTHER INFORMATION: Xaa = Ala, Glu, or Aib
<220> FEATURE:
<221> NAME/KEY: VARIANT
<222> LOCATION: 30
<223> OTHER INFORMATION: Xaa = Glu, Cha, Aib, Acc, or Lys
<220> FEATURE:
<221> NAME/KEY: VARIANT
<222> LOCATION: 31
<223> OTHER INFORMATION: Xaa = Ile, Leu, Cha, Lys, Acc, or deleted
<220> FEATURE:
```

```
<221> NAME/KEY: VARIANT
<222> LOCATION: 32
<223> OTHER INFORMATION: Xaa = His or deleted
<220> FEATURE:
<221> NAME/KEY: VARIANT
<222> LOCATION: 33
<223> OTHER INFORMATION: Xaa = Thr or deleted
<220> FEATURE:
<221> NAME/KEY: VARIANT
<222> LOCATION: 34
<223> OTHER INFORMATION: Xaa = Ala or deleted
<220> FEATURE:
<223> OTHER INFORMATION: This sequence may also encompass a deletion
      peptide with a length of 30, 31, 32 or 33 amino acids

<400> SEQUENCE: 4

Xaa Val Xaa Glu Xaa Gln Xaa Xaa His Xaa Xaa Xaa Lys Xaa Xaa Xaa
 1               5                  10                  15

Xaa Xaa Xaa Arg Arg Xaa Xaa Xaa Xaa Xaa Xaa Xaa Xaa Xaa
            20                  25                  30

Xaa Xaa

<210> SEQ ID NO 5
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Ser, or Dap
<220> FEATURE:
<221> NAME/KEY: VARIANT
<222> LOCATION: 3
<223> OTHER INFORMATION: Xaa = Ser or Aib
<220> FEATURE:
<221> NAME/KEY: VARIANT
<222> LOCATION: 5
<223> OTHER INFORMATION: Xaa = His, Ile, Acc, or Cha
<220> FEATURE:
<221> NAME/KEY: VARIANT
<222> LOCATION: 7
<223> OTHER INFORMATION: Xaa = Leu, Cha, Ile, beta-Nal, Trp, Pal, Acc,
      Phe, or p-X-Phe in which X is OH, a halogen, or CH3
<220> FEATURE:
<221> NAME/KEY: VARIANT
<222> LOCATION: 8
<223> OTHER INFORMATION: Xaa = Leu, Met, Acc, or Cha
<220> FEATURE:
<221> NAME/KEY: VARIANT
<222> LOCATION: 10
<223> OTHER INFORMATION: Xaa = Asp or Asn
<220> FEATURE:
<221> NAME/KEY: VARIANT
<222> LOCATION: 11
<223> OTHER INFORMATION: Xaa = Lys, Leu, Cha, Acc, Phe, or beta-Nal
<220> FEATURE:
<221> NAME/KEY: VARIANT
<222> LOCATION: 12
<223> OTHER INFORMATION: Xaa = Gly, Acc, or Aib
<220> FEATURE:
<221> NAME/KEY: VARIANT
<222> LOCATION: 14
<223> OTHER INFORMATION: Xaa = Ser or His
<220> FEATURE:
<221> NAME/KEY: VARIANT
<222> LOCATION: 15
<223> OTHER INFORMATION: Xaa = Ile, Acc, or Cha
<220> FEATURE:
<221> NAME/KEY: VARIANT
<222> LOCATION: 16
<223> OTHER INFORMATION: Xaa = Gln or Aib
<220> FEATURE:
<221> NAME/KEY: VARIANT
```

```
<222> LOCATION: 17
<223> OTHER INFORMATION: Xaa = Asp or Aib
<220> FEATURE:
<221> NAME/KEY: VARIANT
<222> LOCATION: 18
<223> OTHER INFORMATION: Xaa = Leu, Aib, Acc, or Cha
<220> FEATURE:
<221> NAME/KEY: VARIANT
<222> LOCATION: 19
<223> OTHER INFORMATION: Xaa = Arg or Aib
<220> FEATURE:
<221> NAME/KEY: VARIANT
<222> LOCATION: 22
<223> OTHER INFORMATION: Xaa = Phe, Glu, Aib, Acc, or Cha
<220> FEATURE:
<221> NAME/KEY: VARIANT
<222> LOCATION: 23
<223> OTHER INFORMATION: Xaa = Phe, Leu, Lys, Acc, or Cha
<220> FEATURE:
<221> NAME/KEY: VARIANT
<222> LOCATION: 24
<223> OTHER INFORMATION: Xaa = Leu, Lys, Acc, or Cha
<220> FEATURE:
<221> NAME/KEY: VARIANT
<222> LOCATION: 25
<223> OTHER INFORMATION: Xaa = His, Lys, Aib, Acc, or Glu
<220> FEATURE:
<221> NAME/KEY: VARIANT
<222> LOCATION: 26
<223> OTHER INFORMATION: Xaa = His, Aib, Acc, or Lys
<220> FEATURE:
<221> NAME/KEY: VARIANT
<222> LOCATION: 27
<223> OTHER INFORMATION: Xaa = Leu, Lys, Acc, or Cha
<220> FEATURE:
<221> NAME/KEY: VARIANT
<222> LOCATION: 28
<223> OTHER INFORMATION: Xaa = Ile, Leu, Lys, Acc, or Cha
<220> FEATURE:
<221> NAME/KEY: VARIANT
<222> LOCATION: 29
<223> OTHER INFORMATION: Xaa = Ala, Glu, Acc, or Aib
<220> FEATURE:
<221> NAME/KEY: VARIANT
<222> LOCATION: 30
<223> OTHER INFORMATION: Xaa = Glu, Leu, Nle, Cha, Aib, Acc, or Lys
<220> FEATURE:
<221> NAME/KEY: VARIANT
<222> LOCATION: 31
<223> OTHER INFORMATION: Xaa = Ile, Leu, Cha, Lys, Acc, or deleted
<220> FEATURE:
<221> NAME/KEY: VARIANT
<222> LOCATION: 32
<223> OTHER INFORMATION: Xaa = His or deleted
<220> FEATURE:
<221> NAME/KEY: VARIANT
<222> LOCATION: 33
<223> OTHER INFORMATION: Xaa = Thr or deleted
<220> FEATURE:
<221> NAME/KEY: VARIANT
<222> LOCATION: 34
<223> OTHER INFORMATION: Xaa = Ala or deleted
<220> FEATURE:
<223> OTHER INFORMATION: This sequence may also encompass a deletion
      peptide with a length of 30, 31, 32 or 33 amino acids

<400> SEQUENCE: 5

Xaa Val Xaa Glu Xaa Gln Xaa Xaa His Xaa Xaa Xaa Lys Xaa Xaa Xaa
 1               5                  10                  15

Xaa Xaa Xaa Arg Arg Xaa Xaa Xaa Xaa Xaa Xaa Xaa Xaa Xaa Xaa
            20                  25                  30

Xaa Xaa
```

ANALOGS OF PARATHYROID HORMONE

CROSS REFERENCE TO RELATED APPLICATIONS

This application is a continuation application of U.S. application Ser. No. 11/094,662, filed Mar. 30, 2005, which is a divisional application of U.S. application Ser. No. 10/289,519, filed Nov. 6, 2002, now issued as U.S. Pat. No. 6,921,750, which is a continuation of U.S. application Ser. No. 09/399,499, filed Sep. 20, 1999, now issued as U.S. Pat. No. 6,544,949, which is a continuation-in-part of both U.S. application Ser. No. 08/779,768, filed Jan. 7, 1997, now issued as U.S. Pat. No. 5,969,095 and U.S. application Ser. No. 09/341,217, filed Nov. 22, 1999, now abandoned, which is the national phase application of International Application No. PCT/US97/22498, filed Dec. 8, 1997, which is a continuation-in-part of U.S. application Ser. No. 08/813,534, filed Mar. 7, 1997, now issued as U.S. Pat. No. 5,955,574, which is a continuation-in-part of U.S. application Ser. No. 08/779,768, filed Jan. 7, 1997, now issued as U.S. Pat. No. 5,969,095, which is a continuation-in-part of U.S. application Ser. No. 08/626,186, filed Mar. 29, 1996, now issued as U.S. Pat. No. 5,723,577, which claims the benefit of priority of U.S. Provisional Application No. 60/003,305, filed Sep. 6, 1995 and U.S. Provisional Application No. 60/001,105, filed Jul. 13, 1995. The content of all the prior applications are incorporated herein by reference in their entirety.

BACKGROUND OF THE INVENTION

Parathyroid hormone ("PTH") is a polypeptide produced by the parathyroid glands. The mature circulating form of the hormone is comprised of 84 amino acid residues. The biological action of PTH can be reproduced by a peptide fragment of its N-terminus (e.g. amino acid residues 1 through 34). Parathyroid hormone-related protein ("PTHrP") is a 139 to 173 amino acid-protein with N-terminal homology to PTH. PTHrP shares many of the biological effects of PTH including binding to a common PTH/PTHrP receptor. Tregear, et al., Endocrinal., 93:1349 (1983). PTH peptides from many different sources, e.g., human, bovine, rat, chicken, have been characterized. Nissenson, et al., Receptor, 3:193 (1993).

PTH has been shown to both improve bone mass and quality, Dempster, et al., Endocrine Rev., 14:690 (1993); and Riggs, Amer. J. Med., 91 (Suppl. 5B):37S (1991). The anabolic effect of intermittently administered PTH has been observed in osteoporotic men and women either with or without concurrent antiresorptive therapy. Siovik, et al., J. Bone Miner. Res., 1:377 (1986); Reeve, et al., Br. Med. J., 301:314 (1990); and Hesch, R-D., et al., Calcif. Tissue Int'l, 44:176 (1989).

SUMMARY OF THE INVENTION

In one aspect, the invention features a peptide of the formula (I).

(SEQ ID NO:1)

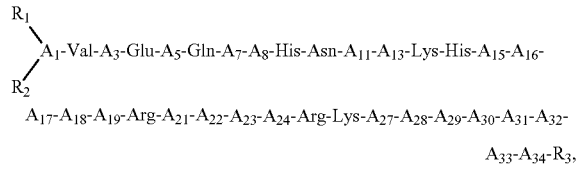

$A_{17}$-$A_{18}$-$A_{19}$-Arg-$A_{21}$-$A_{22}$-$A_{23}$-$A_{24}$-Arg-Lys-$A_{27}$-$A_{28}$-$A_{29}$-$A_{30}$-$A_{31}$-$A_{32}$-

$A_{33}$-$A_{34}$-$R_3$, wherein
$A_1$ is Ser, Ala, or Dap;
$A_2$ is Ser, Thr; or Aib;
$A_5$ is Leu, Nle, Ile, Cha, β-Nat, Trp, Pal, Acc, Phe or p-X-Phe, in which X is OH, a halogen, or $CH_3$;
$A_7$ is Leu, Nle, Ile, Cha, β-Nal, Trp, Pal, Acc, Phe, or p-X-Phe, in which X is OH, a halogen, or $CH_3$;
$A_8$ is Met, Nva, Leu, Val, Ile, Cha, Acc, or Nle;
$A_{11}$ is Leu, Nle, Ile, Cha, β-Nal, Trp, Pal, Acc, Phe or p-X-Phe in which X is OH, a halogen, or $CH_3$;
$A_{12}$ is Gly, Acc, or Aib;
$A_{15}$ is Leu, Nle, Ile, Cha, β-Nal, Trp, Pal, Acc, Phe, or p-X-Phe in which X is OH, a halogen, or $CH_3$;
$A_{16}$ is Ser, Asn, Ala, or Aib;
$A_{17}$ is Ser, Thr, or Aib;
$A_{18}$ is Met, Nva, Leu, Val, Ile, Nle, Acc, Cha, or Aib;
$A_{19}$ is Glu or Aib;
$A_{21}$ is Val, Acc, Cha, or Met;
$A_{22}$ is Acc or Glu;
$A_{23}$ is Trp, Acc, or Cha;
$A_{24}$ is Leu, Acc, or Cha;
$A_{27}$ is Lys, Aib, Leu, hArg, Gln, Acc, or Cha;
$A_{28}$ is Leu, Acc, or Cha;
$A_{29}$ is Gln, Acc, or Aib;
$A_{30}$ is Asp or Lys;
$A_{31}$ is Val, Leu, Nle, Acc, Cha, or deleted;
$A_{32}$ is His or deleted;
$A_{33}$ is Asn or deleted;
$A_{34}$ is Phe, Tyr, Amp, Aib, or deleted;

each of $R_1$ and $R_2$ is, independently, H, $C_{1-12}$ alkyl, $C_{7-20}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxy-phenylalkyl, or $C_{11-20}$ hydroxynaphthylalkyl; and $R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$, or $CONH_2$;

provided that at least one of $A_5$, $A_7$, $A_8$, $A_{11}$, $A_{12}$, $A_{15}$, $A_{18}$, $A_{21}$, $A_{22}$, $A_{23}$, $A_{27}$, $A_{26}$, $A_{29}$, and $A_{31}$ is Acc; or a pharmaceutically acceptable salt thereof.

A preferred embodiment of the immediately foregoing peptide is where $A_3$ is Ser; $A_5$ is Ile or Acc; $A_7$ is Leu, Acc, or Cha; $A_8$ is Acc, Met. Nva, Leu, Val, Ile, or Nle; $A_{11}$ is Leu, Acc, or Cha; $A_{12}$ is Acc or Gly; $A_{15}$ is Leu, Acc, or Cha; $A_{16}$ is Asn or Aib; $A_{17}$ is Ser or Aib; $A_{18}$ is Acc, Met, or Nle; $A_{21}$ is Val or Acc; $A_{27}$ is Lys, hArg, Acc, or Cha; $A_{31}$ is Val, Leu, Nle, Acc, or Cha; $A_{32}$ is His; $A_{33}$ is Asn; $A_{34}$ is Phe, Tyr, Amp, or Aib; or a pharmaceutically acceptable salt thereof.

A preferred embodiment of the immediately foregoing peptide, designated Group B, is where $A_5$ is Ile or Ahc; $A_7$ is Leu, Ahc, or Cha; $A_8$ is Ahc, Met, or Nle; $A_{11}$ is Leu, Ahc, or Cha; $A_{12}$ is Ahc or Gly; $A_{15}$ is Leu, Ahc, or Cha; $A_{18}$ is Met or Ahc; $A_{21}$ is Val or Ahc; $A_{22}$ is Glu or Ahc; $A_{23}$ is Trp, Ahc, or Cha; $A_{24}$ is Leu, Ahc, or Cha; $A_{27}$ is Lys, hArg, Ahc, or Cha; $A_{28}$ is Leu, Ahc, or Cha; $A_{29}$ is Gln, Ahc, or Aib; $A_{31}$ is Val, Leu, Nle, Ahc, or Cha; $R_1$ is H; $R_2$ is H; and $R_3$ is $NH_2$; or a pharmaceutically acceptable salt thereof.

A preferred group of peptides of Group B is where at least one of $A_7$, $A_{11}$, $A_{15}$, $A_{23}$, $A_{24}$, $A_{27}$, $A_{28}$, or $A_{31}$ is Cha.

Another preferred group of peptides of Group B is where at least one of $A_{16}$, $A_{17}$, $A_{19}$, $A_{29}$, or $a_{34}$ is Aib.

Preferred peptides of formula (I) are [Ahc⁷ ¹¹]hPTH(1-34)$NH_2$; [Ahc⁷ ¹¹, Nle⁸ ¹⁸, Tyr³⁴]hPTH(1-34)$NH_2$; [Ahc¹¹]

hPTH(1-34)NH$_2$; [Ahc$^{7\ 11\ 15}$]hPTH(1-34)NH$_2$; [(Ahc$^7$] hPTH(1-34)NH$_2$; [Ahc$^{23}$]hPTH(1-34)NH$_2$; [Ahc$^{24}$]hPTH (1-34)NH$_2$; [Nle$^{8\ 18}$, Ahc$^{27}$]hPTH(1-34)NH$_2$; [Ahc$^{28}$]hPTH (1-34)NH$_2$; [Ahc$^{31}$]hPTH(1-34)NH$_2$; [Ahc$^{24\ 28\ 31}$]hPTH(1-34)NH$_2$; [Ahc$^{24\ 28\ 31}$, Lys$^{30}$]hPTH(1-34)NH$_2$; [Ahc$^{28\ 31}$] hPTH(1-34)NH$_2$; [Ahc$^{15}$]hPTH(1-34)NH$_2$; [Ahc$^{24\ 27}$, Aib$^{29}$, Lys$^{30}$]hPTH(1-34)NH$_2$; [Ahc$^{24\ 27}$, Aib$^{29}$, Lys$^{30}$, Leu$^{31}$] hPTH(1-34)NH$_2$; [Ahc$^5$]hPTH(1-34)NH$_2$; [Ahc$^{12}$]hPTH(1-34)NH$_2$; [Ahc$^{27}$]hPTH(1-34)NH$_2$; [Ahc$^{29}$]hPTH(1-34)NH$_2$; [Ahc$^{24\ 27}$]hPTH(1-34)NH$_2$; [Ahc$^{24\ 27}$, Aib$^{29}$]hPTH(1-34) NH$_2$; [Ahc$^{24}$, Aib$^{29}$]hPTH(1-34)NH$_2$; [Ahc$^{27}$, Aib$^{29}$]hPTH (1-34)NH$_2$; [Ahc$^{18}$]hPTH(1-34)NH$_2$; [Ahc$^8$]hPTH(1-34) NH$_2$; [Ahc$^{18\ 27}$, Aib$^{29}$]hPTH(1-34)NH$_2$; or [Ahc$^{18\ 24\ 27}$, Aib$^{29}$]hPTH(1-34)NH$_2$; [Ahc$^{22}$, Leu$^{27}$, Aib$^{29}$]hPTH(1-34) NH$_2$; [Ahc$^{24}$, Leu$^{27}$, Aib$^{29}$]hPTH(1-34)NH$_2$; [Ahc$^{22}$]hPTH (1-34)NH$_2$; and [Ahc$^{22}$, Aib$^{29}$]hPTH(1-34)NH$_2$; or a pharmaceutically acceptable salt thereof.

The invention also features peptides of the following formulae: [Cha$^{22\ 23}$, Glu$^{25}$, Lys$^{26\ 30}$, Leu$^{28}$, Aib$^{29}$]hPTHrP(1-34)NH$_2$; [Cha$^{22\ 23}$, Glu$^{25}$, Lys$^{26\ 30}$, Aib$^{29}$]hPTHrP(1-34) NH$_2$; [Glu$^{22\ 25}$, Leu$^{23\ 28\ 31}$, Lys$^{26}$, Aib$^{29}$, Nle$^{30}$]hPTHrP(1-34)NH$_2$; [Glu$^{22\ 25}$, Leu$^{23\ 28\ 30\ 31}$, Lys$^{26}$, Aib$^{29}$]hPTHrP(1-34) NH$_2$; [Glu$^{22\ 25\ 29}$, Leu$^{23\ 28\ 30\ 31}$, Lys$^{26}$]hPTHrP(1-34)NH$_2$; [Glu$^{22\ 25\ 29}$, Leu$^{23\ 28\ 31}$, Lys$^{26}$, Nle$^{30}$]hPTHrP(1-34)NH$_2$; [Ser$^1$, Ile$^5$, Met$^8$, Asn$^{10}$, Leu$^{11\ 23\ 28\ 31}$, His$^{14}$, Cha$^{15}$, Glu$^{22\ 25}$, Lys$^{26\ 30}$, Aib$^{29}$]hPTHrP(1-34)NH$_2$; [Glu$^{22\ 25}$, Cha$^{23}$, Lys$^{26}$, Leu$^{28\ 31}$, Aib$^{29}$, Nle$^{30}$]hPTHrP(1-34)NH$_2$; [Cha$^{22\ 23}$, Glu$^{25}$, Lys$^{26\ 30}$, Leu$^{28\ 31}$, Aig$^{29}$]hPTHrP(1-34)NH$_2$; [Cha$^{22}$, Leu$^{23\ 28\ 31}$, Glu$^{25\ 29}$, Lys$^{25}$, Nle$^{30}$]hPTHrP(1-34)NH$_2$; [Cha$^{7\ 11\ 15}$]hPTHrP(1-34)NH$_2$; [Cha$^{7\ 8\ 15}$]hPTHrP(1-34) NH$_2$; [Glu$^{22}$, Cha$^{23}$, Aib$^{25\ 29}$, Lys$^{26\ 30}$, Leu$^{28\ 31}$]hPTHrP(1-34)NH$_2$; [Glu$^{22}$, Cha$^{23}$, Aib$^{25\ 29}$, Lys$^{26}$, Leu$^{28}$]hPTHrP(1-34) NH$_2$; [Glu$^{22}$, Leu$^{23\ 28}$, Aib$^{25\ 29}$, Lys$^{26}$]hPTHrP(1-34)NH$_2$; [Aib$^{29}$]hPTHrP(1-34)NH$_2$; [Glu$^{22\ 25}$, Cha$^{23}$, Lys$^{26}$, Leu$^{28\ 31}$, Aib$^{29}$, Nle$^{30}$]hPTHrP(1-34)NH$_2$; [Glu$^{22\ 25}$, Cha$^{23}$, Lys$^{26\ 30}$, Aib$^{29}$, Leu$^{31}$]hPTHrP(1-34)NH$_2$; [Glu$^{22\ 25}$, Leu$^{23\ 28\ 31}$, Lys$^{26}$, Aib$^{29\ 30}$]hPTHrP(1-34)NH$_2$; [Glu$^{22\ 25}$, Leu$^{23\ 28\ 31}$, Lys$^{26}$, Aib$^{29}$]hPTHrP(1-34)NH$_2$; [Glu$^{22\ 25}$, Leu$^{23\ 28\ 31}$, Aib$^{26\ 29}$, Lys$^{30}$]hPTHrP(1-34)NH$_2$; [Glu$^{22\ 25}$, Cha$^{23}$, Lys$^{26\ 30}$, Leu$^{28\ 31}$, Aib$^{29}$]hPTHrP(1-34)NH$_2$; [Glu$^{22\ 25}$, Cha$^{23}$, Lys$^{26\ 30}$, Aib$^{29}$]hPTHrP(1-34)NH$_2$; [Glu$^{22\ 25}$, Cha$^{23}$, Lys$^{26\ 30}$, Leu$^{28}$, Aib$^{29}$]hPTHrP(1-34)NH$_2$ or [Leu$^{27}$ Aib$^{29}$] hPTH(1-34)NH$_2$; or a pharmaceutically acceptable salt thereof.

The following are examples of the peptides of the invention covered by the above formula: [Glu$^{22\ 25}$, Leu$^{23\ 28}$, Lys$^{26\ 30}$, Aib$^{29}$, Ahc$^{31}$]hPTHrP(1-34)NH$_2$; [Glu$^{22\ 25}$, Ahc$^{23}$, Lys$^{26\ 30}$, Leu$^{28\ 31}$, Aib$^{29}$]hPTHrP(1-34)NH$_2$; [Glu$^{22\ 25}$, Leu$^{23\ 28\ 31}$, Lys$^{26\ 30}$, Ahc$^{27}$, Aib$^{29}$]hPTHrP(1-34)NH$_2$; [Glu$^{22\ 25\ 29}$, Leu$^{23\ 28\ 31}$, Lys$^{26}$, Ahc$^{30}$]hPTHrP(1-34)NH$_2$; [Cha$^{22}$, Leu$^{23\ 28\ 31}$, Glu$^{25}$, Lys$^{26\ 30}$, Ahc$^{27}$, Aib$^{29}$]hPTHrP(1-34)NH$_2$; [Glu$^{22\ 25}$, Leu$^{23\ 28\ 31}$, Ahc$^{24}$, Lys$^{26\ 30}$, Aib$^{29}$]hPTHrP(1-34) NH$_2$; [Glu$^{22\ 29}$, Leu$^{23\ 28\ 31}$, Aib$^{25}$, Lys$^{26\ 30}$, Ahc$^{27}$]hPTHrP (1-34)NH$_2$; [Glu$^{22}$, Leu$^{23\ 28\ 31}$, Aib$^{25\ 29}$, Lys$^{26\ 30}$, Ahc$^{27}$] hPTHrP(1-34)NH$_2$; [Ahc$^{22}$, Leu$^{23\ 28\ 31}$, Glu$^{25}$, Lys$^{26\ 30}$, Aib$^{29}$]hPTHrP(1-34)NH$_2$; [Glu$^{22\ 25}$, Leu$^{23\ 31}$, Lys$^{26\ 30}$, Ahc$^{28}$, Aib$^{29}$]hPTHrP(1-34)NH$_2$; [Cha$^{22}$, Ahc$^{23}$, Glu$^{25}$, Lys$^{26\ 30}$, Leu$^{28\ 31}$, Aib$^{29}$]hPTHrP(1-34)NH$_2$; [Ahc$^{22\ 24\ 27}$, Leu$^{23\ 28\ 31}$, Glu$^{25}$, Lys$^{26\ 30}$, Aib$^{29}$]hPTHrP(1-34)NH$_2$; [Cha$^{22}$, Leu$^{23\ 28\ 31}$, Ahc$^{24\ 27}$, Glu$^{25}$, Lys$^{26\ 30}$, Aib$^{29}$]hPTHrP(1-34)NH$_2$; [Glu$^{22}$, Leu$^{23\ 28\ 31}$, Ahc$^{24\ 27}$, Lys$^{25}$, Leu$^{28}$, Aib$^{29}$(] hPTHrP(1-34)NH$_2$; [Glu$^{22}$, Cha$^{23}$, Ahc$^{24}$, Lyc$^{25}$, Leu$^{28}$, Aib$^{29}$]hPTHrP(1-34)NH$_2$; [Glu$^{22}$, Cha$^{23}$, Ahc$^{24\ 27}$, Lys$^{25}$, Leu$^{28\ 31}$, Lys$^{26}$, Ahc$^{27}$, Aib$^{29}$, Nle$^{30}$]hPTHrP(1-34)NH$_2$; [Ser$^1$, Ile$^5$, Cha$^{7\ 11}$, Met$^8$, Asn$^{10}$, His$^{14}$, Glu$^{22\ 25}$, Leu$^{23\ 28\ 31}$, Lys$^{26\ 30}$, Ahc$^{27}$, Aib$^{29}$]hPTHrP(1-34)NH$_2$; [Ser$^1$, Ile$^5$, Met$^8$, Asn$^{10}$, Leu$^{11\ 23\ 28\ 31}$, His$^{14}$, Cha$^{15}$, Glu$^{22\ 25}$, Lys$^{26\ 30}$, Ahc$^{27}$, Aib$^{29}$] hPTHrP(1-34)NH$_2$; [Cha$^{22}$, Ahc$^{23}$, Glu$^{25}$, Lys$^{26\ 30}$, Leu$^{28\ 31}$, Aib$^{29}$]hPTHrP(1-34)NH$_2$; [Glu$^{22}$, Ahc$^{23}$, Aib$^{25\ 29}$, Lys$^{26\ 30}$, Leu$^{28\ 31}$]hPTHrP(1-34)NH$_2$; [Glu$^{22\ 25}$, Leu$^{23\ 28\ 31}$, Lys$^{26\ 30}$, Ahc$^{29}$]hPTHrP(1-34)NH$_2$; [Cha$^{22}$, Leu$^{23\ 28\ 31}$, Ahc$^{24}$, Glu$^{25}$, Lys$^{26\ 30}$, Aib$^{29}$]hPTHrP(1-34)NH$_2$; [Cha$^{22}$, Leu$^{23\ 28\ 31}$, Ahc$^{24\ 27}$, Glu$^{25}$, Lys$^{26\ 30}$, Aib$^{29}$]hPTHrP(1-34) NH$_2$; [Glu$^{22\ 25}$, Leu$^{23\ 28\ 31}$, Ahc$^{24\ 27}$, Lys$^{26\ 30}$, Aib$^{29}$]hPTHrP (1-34)NH$_2$; [Ahc$^{22\ 24\ 27}$, Leu$^{23\ 28\ 31}$, Glu$^{25}$, Lys$^{26\ 30}$, Aib$^{29}$] hPThrP(1-34)NH$_2$; [Cha$^{22}$, Leu$^{23\ 28\ 31}$, Aib$^{25\ 29}$, Lys$^{26\ 30}$, Ahc$^{27}$]hPTHrP(1-34)NH$_2$; [Ahc$^{22\ 27}$, Leu$^{23\ 28\ 31}$, Aib$^{25\ 29}$, Lys$^{26\ 30}$]hPTHrP(1-34)NH$_2$; [Glu$^{22}$, Leu$^{23\ 28\ 31}$, Ahc$^{24\ 27}$, Lys$^{25\ 26\ 30}$, Aib$^{29}$]hPTHrP 1-34)NH$_2$; [Glu$^{22}$, Leu$^{23\ 25}$, Ahc$^{24\ 27}$, Lys$^{25\ 26\ 30}$, Aib$^{29}$]hPTHrP(1-34)NH$_2$; [Glu$^{22}$, Cha$^{23}$, Ahc$^{24\ 27}$, Lys$^{25\ 25\ 30}$, Leu$^{28}$, Aib$^{29}$]hPTHrP(1-34) NH$_2$; [Glu$^{22\ 25}$, Cha$^{23}$, Ahc$^{24\ 27}$, Lys$^{26\ 30}$, Leu$^{28\ 31}$, Aib$^{29}$] hPTHrP(1-34)NH$_2$; [Glu$^{22}$, Cha$^{23}$, Ahc$^{24\ 27}$, Lys$^{25\ 26\ 30}$, Leu$^{28\ 31}$, Aib$^{29}$]hPTHrP(1-34)NH$_2$; [Glu$^{22}$, Leu$^{23\ 28\ 31}$, Ahc$^{24\ 27}$, Lys$^{25\ 26}$, Aib$^{29}$]hPTHrP(1-34)NH$_2$; [Glu$^{22}$, Leu$^{23\ 28}$, Ahc$^{24\ 27}$, Lys$^{25\ 26}$, Aib$^{29}$]hPTHrP(1-34)NH$_2$; [Glu$^{22}$, Cha$^{23}$, Ahc$^{24\ 27}$, Lys$^{25\ 26}$, Leu$^{28\ 31}$, Aib$^{29}$]hPTHrP(1-34)NH$_2$; [Glu$^{22}$, Cha$^{23}$, Ahc$^{24\ 27}$, Lys$^{25\ 26}$, Leu$^{28}$, Aib$^{29}$] hPTHrP(1-34)NH$_2$; [Glu$^{22}$, Leu$^{23\ 28}$, Lys$^{25\ 26}$, Ahc$^{27}$, Aib$^{29}$]hPTHrP(1-34)NH$_2$; [Glu$^{22}$, Leu$^{23\ 28\ 31}$, Lys$^{25\ 26}$, Ahc$^{27}$, Aib$^{29}$]hPTHrP(1-34)NH$_2$; [Glu$^{22}$, Leu$^{23\ 28\ 31}$, Lys$^{25\ 26\ 30}$, Ahc$^{27}$, Aib$^{29}$]hPTHrP(1-34)NH$_2$; [Glu$^{22}$, Leu$^{23\ 28}$, Lys$^{25\ 26\ 30}$, Ahc$^{27}$, Aib$^{29}$]hPTHRP(1-34)NH$_2$, [Glu$^{22}$, Cha$^{23}$, Ahc$^{24}$, Lys$^{25\ 25}$, Leu$^{28}$, Aib$^{29}$]hPTHrP(1-34)NH$_2$; [Glu$^{22\ 25}$, Leu$^{23\ 28\ 31}$, Lys$^{26}$, Aib$^{29}$, Ahc$^{30}$]hPTHrP(1-34)NH$_2$; [Aib$^{22\ 29}$, Leu$^{23\ 28\ 31}$, Glu$^{25}$, Lys$^{28\ 30}$]hPTHrP(1-34)NH$_2$; [Cha$^{22}$, Ahc$^{23}$, Glu$^{25\ 29}$, Lys$^{26\ 30}$, Leu$^{28\ 31}$]hPTHrP(1-34)NH$_2$; [Cha$^{22}$, Leu$^{23\ 28\ 31}$, Ahc$^{24}$, Glu$^{25\ 29}$, Lys$^{26\ 30}$]hPTHrP(1-34)NH$_2$; [Cha$^{22}$, Leu$^{23\ 28\ 31}$, Glu$^{25\ 29}$, Lys$^{26\ 30}$, Ahc$^{27}$]hPTHrP(1-34) NH$_2$; [Cha$^{22}$, Leu$^{23\ 31}$, Glu$^{25\ 29}$, Lys$^{26\ 30}$, Ahc$^{28}$]hPTHrP(1-34)NH$_2$; [Cha$^{22}$, Leu$^{23\ 28\ 31}$, Glu$^{25\ 29}$, Glu$^{25\ 29}$, Lys$^{26}$, Ahc$^{30}$] hPTHrP(1-34)NH$_2$; [Cha$^{22}$, Leu$^{23\ 28}$, Glu$^{25\ 29}$, Lys$^{26\ 30}$, Ahc$^{31}$, ]hPTHrP(1-34)NH$_2$; [Glu$^{22\ 29}$, Ahc$^{23}$, Aib$^{25}$, Lys$^{26\ 30}$, Leu$^{28\ 31}$, ]hPTHrP(1-34)NH$_2$; [Ahc$^{22}$, Leu$^{23\ 28\ 31}$, Aib$^{25}$, Lys$^{26\ 30}$, Glu$^{29}$]hPTHrP(1-34)NH$_2$; [Glu$^{22\ 29}$, Leu$^{23\ 28\ 31}$, Ahc$^{24}$, Aib$^{25}$, Lys$^{26\ 30}$]hPTHrP(1-34)NH$_2$; [Glu$^{22\ 29}$, Leu$^{23\ 31}$, Aib$^{25}$, Lys$^{26\ 30}$, Ahc$^{28}$]hPTHrP(1-34)NH$_2$; [Glu$^{22\ 29}$, Leu$^{23\ 28}$, Aib$^{25}$, Lys$^{26\ 30}$, Ahc$^{31}$]hPTHrP(1-34) NH$_2$; [Glu$^{22\ 29}$, Leu$^{23\ 28\ 31}$, Aib$^{25}$, Lys$^{25}$, Ahc$^{30}$]hPTHrP(1-34)NH$_2$; [Glu$^{22\ 25\ 29}$, Leu$^{23\ 28\ 31}$, Lys$^{26}$, Ahc$^{27}$, Aib$^{30}$] hPTHrP(1-34)NH$_2$; [Glu$^{22\ 25\ 29}$, Leu$^{23\ 28\ 31}$, Ahc$^{24}$, Lys$^{26}$, Aib$^{30}$] hPTHrP(1-34)NH$_2$; [Ahc$^{22}$, Leu$^{23\ 28\ 31}$, Glu$^{25\ 29}$, Lys$^{26}$, Aib$^{30}$]hPTHrP(1-34)NH$_2$; [Ahc$^{22}$, Leu$^{23\ 28}$, Glu$^{25\ 29}$, Lys$^{26\ 30\ 31}$]hPTHrP(1-34)NH$_2$; [Glu$^{22\ 25\ 29}$, Leu$^{23\ 28}$, Lys$^{26\ 31}$, Ahc$^{30}$]hPTHrP(1-34)NH$_2$; [Glu$^{22\ 25\ 29}$, Leu$^{23\ 28}$, Lys$^{26\ 30\ 31}$, Ahc$^{27}$]hPTHrP(1-34)NH$_2$; [Ahc$^{22}$, Cha$^{23}$, Glu$^{25}$, Lys$^{28\ 30}$, Leu$^{28\ 31}$, Aib$^{29}$]hPTHrP(1-34)NH$_2$; [Ahc$^{22}$, Cha$^{23}$, Lys$^{25\ 26\ 30}$, Leu$^{28\ 31}$, Leu$^{28\ 31}$, Aib$^{29}$]hPTHrP(1-34)NH$_2$; [Ahc$^{22}$, Cha$^{23}$, Lys$^{25\ 26}$, Leu$^{28\ 31}$, Aib$^{29}$]hPTHrP(1-34)NH$_2$; [Ahc$^{22}$, Leu$^{23\ 28}$, Lys$^{25\ 26}$, Aib$^{29}$]hPTHrP(1-34)NH$_2$; [Ahc$^{22}$, Leu$^{23\ 28}$, Arg$^{25}$, Lys$^{26}$, Aib$^{29}$]hPTHrP(1-34)NH$_2$; [Ahc$^{22\ 24}$, Leu$^{23\ 28\ 31}$, Glu$^{25}$, Lys$^{28\ 30}$, Aib$^{29}$]hPTHrP(1-34)NH$_2$; [Ahc$^{22\ 24}$, Leu$^{23\ 28\ 31}$, Lys$^{25\ 26\ 30}$, Aib$^{29}$]hPTHrP(1-34)NH$_2$; [Ahc$^{22\ 24}$, Leu$^{23\ 28\ 31}$, Lys$^{25\ 25}$, Aib$^{29}$]hPTHrP(1-34)NH$_2$; [Ahc$^{22\ 24}$, Leu$^{23\ 28}$, Lys$^{25\ 26}$, Aib$^{29}$]hPTHrP(1-34)NH$_2$; [Ahc$^{22\ 24}$, Leu$^{23\ 28}$, Arg$^{25}$, Lys$^{26}$, Aib$^{29}$]hPTHrP(1-34)NH$_2$; [Glu$^{22}$, Leu$^{23\ 28\ 31}$, Ahc$^{24}$, Lys$^{25\ 26\ 30}$, Aib$^{29}$]hPTHrP(1-34) NH$_2$; [Glu$^{22}$, Leu$^{23\ 28\ 31}$, Ahc$^{24}$, Lys$^{25\ 26}$, Aib$^{29}$]hPTHrP(1-34)NH$_2$; [Glu$^{22}$, Leu$^{23\ 28}$, Ahc$^{24}$, Lys$^{25\ 26}$, Aib$^{29}$]hPTHrP(1-34)NH$_2$; [Glu$^{22}$, Leu$^{23\ 28\ 31}$, Ahc$^{24}$, Arg$^{25}$, Lys$^{26\ 30}$, Aib$^{29}$] hPTHrP(1-34)NH$_2$; [Glu$^{22}$, Leu$^{23\ 28\ 31}$, Ahc$^{24}$, Arg$^{25}$, Lys$^{28}$, Aib$^{29}$]hPTHrP(1-34)NH$_2$; [Glu$^{22}$, Leu$^{23\ 28}$, Ahc$^{24}$, Arg$^{25}$, Lys$^{26}$, Aib$^{29}$]hPTHrP(1-34)NH$_2$; [Glu$^{22}$, Ahc$^{23}$, Aib$^{25\ 29}$, Lys²⁶ ³⁰, Leu²⁸ ³¹,]hPTHrP(1-34)NH₂; [Glu²², Ahc²³, Aib²⁵ ²⁹, Lys²⁶, Leu²⁸]hPTHrP(1-34)NH₂; [Glu²², Ahc²³ ³¹, Aib²⁵ ²⁹, Lys²⁶, Leu²⁸]hPTHrP(1-34)NH₂; [Glu²², Leu²³ ²⁸, Aib²⁵ ²⁹, Lys²⁶ ³⁰, Ahc³¹]hPTHrP(1-34)NH₂; [Glu²², Leu²³ ²⁸, Aib²⁵ ²⁹, Lys²⁶, Ahc³¹]hPTHrP(1-34)NH₂; [Glu²² ²⁵, Leu²³ ²⁵, Ahc²⁴ ³¹, Lys²⁶ ³⁰, Aib²⁹]hPTHrP(1-34)NH₂; or [Glu²², Leu²³ ²⁸, Ahc²⁴ ³¹, Lys²⁵ ²⁶, Aib²⁹]hPTHrP(1-34)NH₂; [Glu²², Leu²³ ²⁸ ³¹, Ahc²⁴, Aib²⁵ ²⁹, Lys²⁶ ³⁰]hPTHrP(1-34)NH₂; or a pharmaceutically acceptable salt thereof.

In another aspect, the invention relates to peptide variants of PTH(1-34) of the following generic formula:

(SEQ ID NO:2)

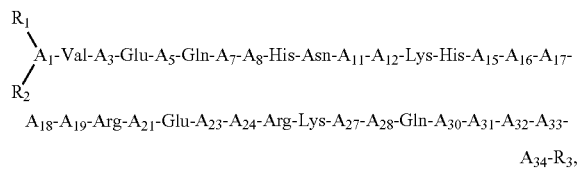

wherein
A₂ is Ser, Ala, or Dap;
A₃ is Ser, Thr, or Aib;
A₅ is Leu, Nle, Ile, Cha, β-Nal, Trp, Pal, Phe or p-X-Phe, in which X is OH, a halogen or CH₃;
A₇ is Leu, Nle, Ile, Cha, β-Nal, Trp, Pal, Phe, or p-X-Phe in which X is OH, a halogen, or CH₃;
A₈ is Met, Nva, Leu, Val, Ile, Cha, or Nle;
A₁₁ is Leu, Nle, Ile, Cha, β-Nal, Trp, Pal, Phe or p-X-Phe in which X is OH, a halogen or CH₃;
A₁₂ is Gly or Aib;
A₁₅ is Leu, Nle, Ile, Cha, β-Nal, Trp Pal, Phe, or p-X-Phe in which X is OH, a halogen, or CH₃;
A₁₆ is Ser, Asn, Ala or Aib;
A₁₇ is Ser, Thr, or Aib;
A₁₈ is Met, Nva, Leu, Val, Ile, Nle, Cha or Aib;
A₁₉ is Glu or Aib;
A₂₁ is Val, Cha, or Met;
A₂₃ is Trp or Cha;
A₂₄ is Leu or Cha;
A₂₇ is Lys, Aib, Leu, hArg, Gln, or Cha;
A₂₈ is Leu or Cha;
A₃₀ is Asp or Lys;
A₃₁ is Val, Nle, Cha, or deleted;
A₃₂ is His or deleted;
A₃₃ is Asn or deleted;
A₃₄ is Phe, Tyr, Amp, Aib or deleted;
each of R₁ and R₂ is, independently, H, C₁₋₁₂ alkenyl, C₂₋₁₂ alkenyl, C₇₋₂₀ phenylalkyl, C₁₁₋₂₀ naphthylalkyl, C₁₋₁₂ hydroxyalkyl, C₂₋₁₂ hydroxyalkenyl, C₇₋₂₀ hydroxyphenylalkyl, or C₁₁₋₂₀ hydroxynaphthylalkyl; or one and only one of R₁ and R₂ is COE₁ in which E₁ is C₁₋₁₂ is alkyl, C₂₋₁₂ alkenyl, C₇₋₂₀ phenylalkyl, C₁₁₋₂₀ naphthylalkyl, C₁₋₁₂ hydroxyalkyl, C₂₋₁₂ hydroxyalkenyl, C₇₋₂₀ hydroxy-phenylalkyl, or C₁₁₋₂₀ hydroxynaphthylalkyl; and
R₃ is OH, NH₂, C₁₋₁₂ alkoxy, or NH—Y—CH₂—Z in which Y is a C₁₋₁₂ hydrocarbon moiety and Z is H, OH, CO₂H, or CONH₂;
provided that (i) at least one of A₅, A₇, A₈, A₁₁, A₁₅, A₁₈, A₂₁, A₂₃, A₂₄, A₂₇, A₂₈, and A₃₁ is Cha, or at least one of A₃, A₁₂, A₁₅, A₁₇, A₁₈, A₁₉, and A₃₄ is Aib; or that (ii) at least A₁ is Dap, A₇ is β-Nal, Trp, Pal, Phe, or p-X-Phe, A₁₅ is β-Nal, Trp, Pal, Phe, or p-X-Phe, A₂₇ is hArg, or A₃₁ is Nle; or a pharmaceutically acceptable salt thereof.

In another aspect, the invention relates to peptide variants of PTH(1-34) of the following formula (II):

(SEQ ID NO:2)

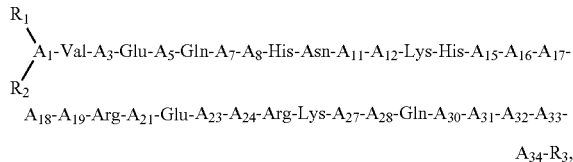

wherein
A₁ is Ser, Ala, or Dap;
A₃ is Ser, Thr or Aib;
A₅ is Leu, Nle, Ile, Cha, β-Nal, Trp, Pal, Phe or p-X-Phe, in which X is OH, a halogen, or CH₃;
A₇ is Leu, Nle, Ile, Cha, β-Nal, Trp, Pal, Phe, or p-X-Phe in which X is OH, a halogen, or CH₃;
A₈ is Mel, Nva, Leu, Val, Ile, Cha, or Nle;
A₁₁ is Leu, Nle, Ile, Cha, β-Nal, Trp, Pal, Phe or p-X-Phe in whic X is OH, a halogen, or CH₃;
A₁₂ is Gly or Aib;
A₁₅ is Leu, Nle, Ile, Cha, β-Nal, Trp, Pal, Phe or p-X-Phe in which X is OH, a halogen, or CH₃;
A₁₆ is Ser, Asn, Ala, or Aib;
A₁₇ is Ser, Thr, or Aib;
A₁₈ is Met, Nva, Leu, Val, Ile, Nle, Cha, or Aib;
A₁₉ is Glu or Aib;
A₂₁ is Val, Cha, or Met;
A₂₃ is Trp or Cha;
A₂₄ is Leu or Cha;
A₂₇ is Lys, Aib, Leu, hArg, Gln, or Cha;
A₂₈ is Leu or Cha;
A₃₀ is Asp or Lys;
A₃₁ is Val, Nle, Cha, or deleted;
A₃₂ is His or deleted;
A₃₃ is Asn or deleted;
a₃₄ is Phe, Tyr, Amp, Aib, or deleted;
each of R₁ and R₂ is, independently, H, C₁₋₁₂ alkenyl, C₇₋₂₀ phenylalkyl, C₁₁₋₂₀ naphthylalkyl, C₁₋₁₂ hydroxyalkyl, C₂₋₁₂ hydroxyalkenyl, C₇₋₂₀ hydroxyphenylalkyl, or C₁₁₋₂₀ hydroxynaphthylalkyl; or one and only one of R₁ and R₂ is COE₁ in which E₁ is C₁₋₁₂ alkyl C₂₋₁₂ alkenyl, C₇₋₂₀ phenylalkyl, C₁₁₋₂₀ naphthylalkyl, C₁₋₁₂ hydroxyalkyl, C₂₋₁₂ hydroxyalkenyl, C₇₋₂₀ hydroxy-phenylalkyl, or C₁₁₋₂₀ hydroxynaphthylalkyl; and
R₃ is OH, NH₂, C₁₋₁₂ alkoxy, or NH—Y—CH₂—Z in which Y is a C₁₋₁₂ hydrocarbon moiety and Z is H, OH, CO₂H, or CONH₂;
provided that (i) at least one of A₅, A₇, A₈, A₁₁, A₁₅, A₁₈, A₂₁, A₂₃, A₂₄, A₂₇, A₂₈, and A₃₁ is Cha, or at least one of A₃, A₁₂, A₁₆, A₁₇, A₁₈, A₁₉, and a₃₄ is Aib; and the peptide is not [Aib¹², Tyr³⁴]hPTH(1-34)NH₂, or a pharmaceutically acceptable salt thereof.

A preferred group of peptides of formula (II), designated Group (i) is where at least one of A₇, a₁₁, A₁₅, A₂₃, A₂₄, A₂₇, A₂₈, and A₃₁ is Cha; or a pharmaceutically acceptable salt thereof.

A preferred group of peptides of Group (i), designated Group (ii) is where A₃ is Ser; A₅ is Ile; A₇ is Leu or Cha; A₈ is Met, Nva, Leu, Val, Ile, or Nle; A₁₁ is Leu or Cha; A₁₂ is Gly;

$A_{15}$ is Leu or Cha; $A_{16}$ is Asn or Aib; $A_{17}$ is Ser; $A_{18}$ is Met or Nle; $A_{21}$ is Val; $A_{27}$ is Lys, hArg, or Cha; $A_{32}$ is His; $A_{31}$ is Val, Nle, or Cha; $A_{33}$ is Asn; $A_{34}$ is Phe, Tyr, amp, or Aib; $R_1$ is H; $R_2$ is H; and $R_3$ is $NH_2$; or a pharmaceutically acceptable salt thereof.

A preferred group of peptides of Group (ii), designated Group (iii), is where at least one of $A_7$ and $A_{11}$ is Cha; or a pharmaceutically acceptable salt thereof.

Preferred peptides of Group (iii) are [Cha$^{7\ 11}$]hPTH(1-34)NH$_2$, [Cha$^{7\ 11}$, Nle$^{8\ 18}$, Tyr$^{34}$]hPTH(1-34)NH$_2$; [Cha$^{11}$]hPTH(1-34)NH$_2$; [Cha$^{7\ 11\ 15}$]hPTH(1-34)NH$_2$; and [Cha$^7$]hPTH(1-34)NH$_2$; or a pharmaceutically acceptable salt thereof.

Another preferred group of peptides of Group (ii), designated Group (iv), is where at least one of $A_{15}$, $A_{23}$, $A_{24}$, $A_{27}$, $A_{28}$, and $A_{31}$ is Cha; or a pharmaceutically acceptable salt thereof.

Preferred peptides of Group (iv) are [Cha$^{23}$]hPTH(1-34)NH$_2$, [Cha$^{24}$]hPTH(1-34)NH$_2$, [Nle$^{8\ 18}$, Cha$^{27}$]hPTH(1-34)NH$_2$, [Cha$^{28}$]hPTH(1-34)NH$_2$, [Cha$^{31}$]hPTH(1-34)NH$_2$, [Cha$^{24\ 28\ 31}$]hPTH(1-34)NH$_2$; [Cha$^{24\ 28\ 31}$, Lys$^{30}$]hPTH(1-34)NH$_2$; [Cha$^{28\ 31}$]hPTH(1-34)NH$_2$; and [Cha$^{15}$]hPTH(1-34)NH$_2$; or a pharmaceutically acceptable salt thereof.

Another preferred group of peptides of formula (II), designated Group (v), is where at least one of $A_3$, $A_{12}$, $A_{16}$, $A_{17}$, $A_{18}$, $A_{19}$, and $A_{34}$ is Aib; or a pharmaceutically acceptable salt thereof.

A preferred group of peptides of Group (v), designated Group (vi), is where $A_3$ is Ser or Aib; $A_5$ is Ile; $A_7$ is Leu or Cha; $A_8$ is Met, Nva, Leu, Val, Ile, or Nle; $A_{11}$ is Leu or Cha; $A_{15}$ is Leu or Cha; $A_{15}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe, Tyr, Amp, or Aib; $R_1$ is H; $R_2$ is H; and $R_3$ is $NH_2$ or a pharmaceutically acceptable salt thereof.

A preferred group of peptides of Group (vi), designated Group (vii), is where at least one of $A_3$, $A_{12}$, $A_{16}$, $A_{17}$, $A_{19}$, and $A_{34}$ is Aib; or a pharmaceutically acceptable salt thereof.

Preferred peptides of Group (vii) are [Aib$^{16}$]hPTH(1-34)NH$_2$, [Aib$^{19}$]hPTH(1-34)NH$_2$, [Aib$^{34}$]hPTH(1-34)NH$_2$; [Aib$^{15\ 19}$]hPTH(1-34)NH$_2$; [Aib$^3$]hPTH(1-34)NH$_2$; [Aib$^{17}$]hPTH(1-34)NH$_2$; and [Aib$^{12}$]hPTH(1-34)NH$_2$; or a pharmaceutically acceptable salt thereof.

Another preferred group of peptides of formula (II), designated Group (viii), is where at least one of $A_7$, $A_{11}$, $A_{15}$, $A_{23}$, $A_{24}$, $A_{27}$, $A_{28}$, and $A_{31}$ is Cha and at least one of $A_3$, $A_{12}$, $A_{16}$, $A_{17}$, $A_{18}$, $A_{19}$, and $a_{34}$ is Aib; or a pharmaceutically acceptable salt thereof.

A preferred group of peptides of Group (viii), designated Group (ix), is where $A_3$ is Ser or Aib; $A_5$ is Ile; $A_7$ is Leu or Cha; $A_8$ is Met, Nva, Leu, Val, Ile, or Nle; $a_{11}$ is Leu or Cha; $A_{15}$ is Leu or Cha; $A_{16}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe, Tyr, Amp, or Aib; $R_1$ is H; $R_2$ is H; and $r_3$ is $NH_2$; or a pharmaceutically acceptable salt thereof.

A preferred group of peptides of Group (ix), designated Group (x), is where at least one of $A_7$ and $A_{11}$ is Cha and at least one of $A_{16}$, $A_{19}$, and $A_{34}$ is Aib; or a pharmaceutically acceptable salt thereof.

Preferred peptides of Group (x) are [Cha$^{7\ 11}$, Nle$^{8\ 18}$, Aib$^{16\ 19}$, Tyr$^{34}$]hPTH(1-34)NH$_2$, [Cha$^{7\ 11}$, Nle$^{8\ 18\ 31}$, Aib$^{16\ 19}$, Tyr$^{34}$]hPTH(1-34)NH$_2$, [Cha$^{7\ 11}$, Aib$^{19}$]hPTH(1-34)NH$_2$, [Cha$^{7\ 11}$, Aib$^{16}$]hPTH(1-34)NH$_2$; [Cha$^{7\ 11}$, Nle$^{8\ 18}$, Aib$^{34}$]hPTH(1-34)NH$_2$; or [Cha$^{7\ 11}$, Aib$^{19}$, Lys$^{30}$]hPTH(1-34)NH$_2$; or a pharmaceutically acceptable salt thereof.

Another preferred group of peptides of Group (ix), designated Group (xi), is where at least one of $A_{24}$, $A_{28}$, and $A_{31}$ is Cha and at least one of $A_{15}$ and $A_{17}$ is Aib; or a pharmaceutically acceptable salt thereof.

Preferred peptides of Group (xi) are [Cha$^{28}$, Nle$^{8\ 18}$, Aib$^{16\ 19}$, Tyr$^{34}$]hPTH(1-34)NH$_2$, and [Cha$^{28}$, Aib$^{18\ 19}$]PTH(1-34)NH$_2$; or a pharmaceutically acceptable salt thereof.

In another aspect, the present invention is directed to a peptide of the formula (III):

(SEQ ID NO:2)

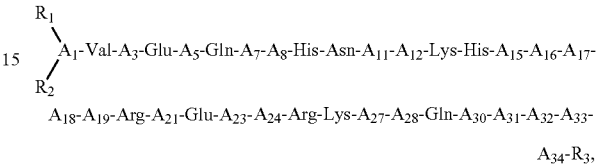

wherein
$A_1$ is Ser, Ala or Dap;
$A_3$ is Ser, Thr, or Aib;
$A_5$ is Leu, Nle, Cha, β-Nal, Trp, Pal, Phe or p-X-Phe, in which X is OH, a halogen, or $CH_3$;
$A_7$ is Leu, Nle, Cha, β-Nal, Trp, Pal, Phe, or p-X-Phe in which X is H, OH, a halogen, or $CH_3$;
$A_8$ is Met, Nva, Leu, Val, Ile, Cha, or Nle;
$A_{11}$ is Leu, Nle, Ile, Cha, β-Nal, Trp, Pal, Phe or p-X-Phe in which X is OH, a halogen, or $CH_3$;
$A_{12}$ is Gly or Aib;
$A_{15}$ is Leu, Nle, Ile, Cha, β-Nal, Trp, Pal, Phe, or p-X-Phe in which X is OH, a halogen, or $CH_3$;
$A_{16}$ is Ser, Asn, Ala, or Aib;
$A_{17}$ is Ser, Thr, or Aib;
$A_{18}$ is Met, Nva, Leu, Val, Ile, Nle, Cha, or Aib;
$A_{19}$ is Glu or Aib;
$A_{21}$ is Val, Cha, or Met;
$A_{23}$ is Trp or Cha;
$A_{24}$ is Leu or Cha;
$A_{27}$ is Lys, Aib, Leu, hArg, Gln, or Cha;
$A_{28}$ is Leu or Cha;
$A_{30}$ is Asp or Lys;
$a_{31}$ is Val, Nle, Cha, or deleted;
$A_{32}$ is His or deleted;
$A_{33}$ Asn or deleted;
$A_{34}$ is Phe, Tyr, Amp, Aib, or deleted;
each of $R_1$ and $R_2$ is, independently, H, $C_{1-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxy-phenylalkyl, or $C_{11-20}$ hydroxynaphthylalkyl;
$R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$, or $CONH_2$;
provided that at least $A_1$ is Dap, $A_7$ is β-Nal, Trp, Pal, Phe, or p-X-Phe; $A_{15}$ is β-Nal, Trp, Pal, Phe, or p-X-Phe, $A_{27}$ is hArg, or $A_{31}$ is Nle; or a pharmaceutically acceptable salt thereof.

A preferred group of peptides of formula (III) is where $A_1$ is Ser, Gly, or Dap; $A_3$ is Ser or Aib; $A_8$ is Met, Nva, Leu, Val, Ile, or Nle; $A_{18}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe; Tyr, Amp, or Aib; $R_1$ is H; $R_2$ is H; and $R_3$ is $NH_2$; or a pharmaceutically acceptable salt thereof.

Preferred peptides of the immediately foregoing peptides are [$Nle^{31}$]hPTh(1-34)$NH_2$; [$hArg^{27}$]hPTH(1-34)$NH_2$, and [$Dap^1 Nle^{8,18}, Tyr^{34}$]hPTH(1-34)$NH_2$; or a pharmaceutically acceptable salt thereof.

In another aspect, the present invention is directed to a peptide of the formula (IV):

(SEQ ID NO:3)

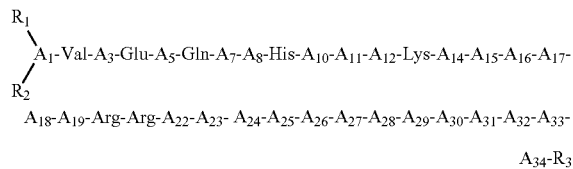

wherein
$A_2$ is Ala, Ser, or Dap;
$A_3$ is Ser or Aib;
$A_5$ is His, Ile, or Cha;
$A_7$ is Leu, Cha, Nle, β-Nal, Trp, Pal, Phe, or p-X-Phe in which X is OH, a halogen, or $CH_3$;
$A_8$ is Leu, Met, or Cha;
$A_{10}$ is Asp or Asn;
$A_{11}$ is Lys, Leu, Cha, Phe, or β-Nal;
$A_{12}$ is Gly or Aib;
$A_{14}$ is Ser or His;
$A_{15}$ is Ile, or Cha;
$A_{16}$ is Gln or Aib;
$A_{17}$ is Asp or Aib;
$A_{18}$ is Leu, Aib, or Cha;
$A_{19}$ is Arg or Aib;
$A_{22}$ is Phe, Glu, Aib, or Cha;
$A_{23}$ is Phe, Leu, Lys, or Cha;
$A_{24}$ is Leu, Lys, or Cha;
$A_{25}$ is His, Aib, or Glu;
$A_{26}$ is His, Aib, or Lys;
$A_{27}$ is Leu, Lys, or Cha;
$A_{28}$ is Ile, Leu, Lys, or Cha;
$A_{29}$ is Ala, Glu, or Aib;
$A_{30}$ is Glu, Cha, Aib, or Lys;
$A_{31}$ is Leu, Cha, Lys, or deleted;
$A_{32}$ is His or deleted;
$A_{33}$ is Thr or deleted;
$A_{34}$ is Ala or deleted;
each of $R_1$ and $R_2$ is, independently, H, $C_{1-12}$ alkanyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; and
$R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$ or $CONH_2$;
provided that at least one of $A_5$, $A_7$, $A_8$, $A_{11}$, $A_{15}$, $A_{18}$, $A_{22}$, $A_{23}$, $A_{24}$, $A_{27}$, $A_{28}$, $A_{30}$, or $A_{31}$ is Cha or at least one of $A_3$, $A_{12}$, $A_{16}$, $A_{17}$, $A_{18}$, $A_{19}$, $A_{22}$, $A_{25}$, $A_{26}$, $A_{29}$, $A_{30}$, or $A_{34}$ is Aib; or a pharmaceutically acceptable salt thereof.

A preferred group of peptides of formula (V) is where $A_{22}$ is Phe or Cha; $A_{23}$ is Phe or Cha; $A_{25}$ is His; $A_{26}$ is His; $A_{27}$ is Leu or Cha; $A_{29}$ is Ala; $A_{30}$ is Glu or Lys; $A_{31}$ is Ile or Cha; $A_{32}$ is His; $A_{33}$ is Thr; and $A_{34}$ is Ala; or a pharmaceutically acceptable salt thereof. Two preferred groups of peptides of the immediately foregoing group of peptides is where at least one of $A_7$ and $A_{11}$ is Cha; or where at least one of $A_{15}$ or $A_{19}$ is Aib; or a pharmaceutically acceptable salt thereof.

Another preferred group of peptides of formula (IV), is where $A_{22}$ is Glu, Aib, or Cha; $A_{23}$ is Leu, Lys, or Cha; $A_{25}$ is Aib or Glu; $A_{25}$ is Aib or Lys; $A_{28}$ is Leu, Lys, or Cha; $A_{29}$ is Glu or Aib; $A_{30}$ is Cha, Aib, or Lys; $A_{31}$ is Leu, Cha, or Lys; $A_{32}$ is His; $A_{33}$ is Thr; and $A_{34}$ is Ala; or a pharmaceutically acceptable salt thereof. Two preferred groups of peptides of the immediately foregoing group of peptides is where at least one of $A_7$ and $A_{11}$ is Cha; or where at least one of $A_{16}$ or $A_{19}$ is Aib; or a pharmaceutically acceptable salt thereof.

In another aspect, this invention is directed to a peptide of the formula (V):

(SEQ ID NO:4)

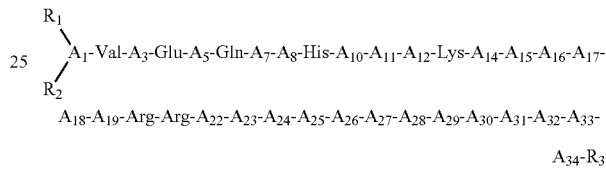

wherein
$A_1$ is Ala, Ser or Dap;
$A_3$ is Ser or Aib;
$A_5$ is His, Ile or Cha;
$A_7$ is Leu, Cha, Nle, η-Nal, Trp, Pal, Phe, or p-X-Phe in which X is OH, a halogen or $CH_3$;
$A_8$ is Leu, Met or Cha;
$A_{10}$ is Asp or Asn;
$A_{11}$ is Lys, Leu, Cha, Phe or β-Nal;
$A_{12}$ is Gly or Aib;
$A_{14}$ is Ser or His;
$A_{15}$ is Ile or Cha;
$A_{16}$ is Gln or Aib;
$A_{17}$ is Asp or Aib;
$A_{18}$ is Leu, Aib or Cha;
$A_{19}$ is Arg or Aib;
$A_{22}$ is Phe, Glu, Aib, Acc or Cha;
$A_{23}$ is Phe, Leu, Lys, Acc or Cha;
$A_{24}$ is Leu, Lys, Acc or Cha;
$A_{25}$ is His, Aib or Glu;
$A_{25}$ is His, Aib or Lys;
$A_{27}$ is Leu, Lys, Acc or Cha;
$A_{28}$ is Ile, Leu, Lys, Acc or Cha;
$A_{29}$ is Ala, Glu or Aib;
$A_{30}$ is Glu, Cha, Aib, Acc or Lys;
$A_{31}$ is Ile, Leu, Cha, Lys, Acc or deleted;
$A_{32}$ is His or deleted;
$A_{33}$ is Thr or deleted;
$A_{34}$ is Ala or deleted;
each of $R_1$ and $R_2$ is, independently, H, $C_{1-12}$ alkanyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; and $R_3$ is OH, $NH_2$, $C_{1-12}$ alkoxy, or NH—Y—CH$_2$—Z in which Y is a $C_{1-12}$ hydrocarbon moiety and Z is H, OH, $CO_2H$ or $CONH_2$;

provided that at least one of $A_{23}$, $A_{24}$, $A_{27}$, $A_{28}$, or $A_{31}$ is Lys; or a pharmaceutically acceptable salt thereof.

A preferred group of peptides of formula (V) is where $A_{22}$ is Glu, Aib, Acc, or Cha; $A_{23}$ is Leu, Lys, Acc or Cha; $A_{25}$ is Aib or Glu; $A_{26}$ is Aib or Lys; $A_{28}$ is Leu, Lys, Acc, or Cha; $A_{29}$ is Glu or Aib; $A_{30}$ is Cha, Aib, Acc, or Lys; $A_{31}$ is Leu, Cha, Acc, or Lys; $A_{32}$ is His; $A_{32}$ is Thr; and $A_{34}$ Ala; or a pharmaceutically acceptable salt thereof. Two preferred groups of peptides of the immediately foregoing group of peptides is where at least one of $A_7$ and $A_{11}$ is Cha; or where at least one of $A_{16}$ or $A_{19}$ is Aib; or a pharmaceutically acceptable salt thereof.

The following are examples of peptides of this invention as encompassed by formula (II): [Cha$^7$]hPTH(1-34)NH$_2$; [Cha$^{11}$]hPTH(1-34)NH$_2$; [Cha$^{15}$]hPTH(1-34)NH$_2$; [Cha$^{7\,11}$]hPTH(1-34)NH$_2$; [Cha$^{7\,11}$, Nle$^{8\,18}$, Tyr$^{34}$]hPTH(1-34) NH$_2$; [Cha$^{23}$]hPTH(1-34)NH$_2$; [Cha$^{24}$]hPTH(1-34)NH$_2$; [Nle$^{8\,18}$, Cha$^{27}$;]hPTH(1-34)NH$_2$; [Cha$^{28}$]hPTH(1-34)NH$_2$; [Cha$^{27\,29}$]hPTH(1-34)NH$_2$; [Cha$^{27}$]hPTH(1-34)NH$_2$; [Cha$^{27\,29}$]hPTH(1-34)NH$_2$; [Cha$^{28}$]bPTH(1-34)NH$_2$; [Cha$^{28}$]rPTH(1-34)NH$_2$; [Cha$^{24\,28\,31}$]hPTH(1-34)NH$_2$; [Aib$^{15}$]hPTH(1-34)NH$_2$; [Aib$^{19}$]hPTH(1-34)NH$_2$; [Aib$^{34}$]hPTH(1-34)NH$_2$; [Aib$^{16\,19}$]hPTH(1-34)NH$_2$; [Aib$^{16\,19\,34}$]bPTH(1-34)NH$_2$; [Aib$^{16\,34}$]hPTH(1-34)NH$_2$; [Aib$^{19\,34}$]hPTH(1-34)NH$_2$; [Cha$^{7\,11}$, Nle$^{8\,18}$, Aib$^{16\,19}$, Tyr$^{34}$]hPTH(1-34)NH$_2$; [Cha$^{7\,11}$, Nle$^{8\,18\,31}$, Aib$^{16\,19}$, Tyr$^{34}$]hPTH(1-34)NH$_2$; [Cha$^7$, Aib$^{16}$]hPTH(1-34)NH$_2$; [Cha$^{11}$, Aib$^{16}$]hPTH(1-34)$_2$; [Cha$^7$, Aib$^{34}$]hPTH(1-34)NH$_2$; [Cha$^{11}$, Aib$^{34}$]hPTH(1-34)NH$_2$; [Cha$^{27}$, Aib$^{15}$]hPTH(1-34)NH$_2$; [Cha$^{27}$, Aib$^{34}$]hPTH(1-34)NH$_2$; [Cha$^{28}$, Aib$^{16}$]hPTH(1-34)NH$_2$; [Cha$^{28}$, Aib$^{34}$]hPTH(1-34)NH$_2$; [Nle$^{31}$]hPTH(1-34)NH$_2$; [hArg$^{27}$]hPTH(1-34)NH$_2$; [Dap$^1$, Nle$^{8\,18}$, Tyr$^{34}$]hPTH(1-34)NH$_2$; [NLE$^{31}$]bPTH(1-34)NH$_2$; [Nle$^{31}$]rPTH(1-34)NH$_2$; [hArg$^{27}$]bPTH(1-34)NH$_2$; [hArg$^{27}$]rPTH(1-34)NH$_2$; [Cha$^{7\,11}$, Aib$^{19}$, Lys$^{30}$]hPTH(1-34)NH$_2$; [Aib$^{12}$]hPTH(1-34)NH$_2$; [Cha$^{24\,28\,31}$, Lys$^{30}$]hPTH(1-34)NH$_2$; [Cha$^{28\,31}$]hPTH(1-34)NH$_2$; [Cha$^{7\,11}$, Nle$^{8\,18}$, Aib$^{34}$]hPTH(1-34)NH$_2$; [Aib$^3$]hPTH(1-34)NH$_2$; [Cha$^8$]hPTH(1-34)NH$_2$; [Cha$^{15}$]hPTH(1-34)NH$_2$; [Cha$^{7\,11}$, Aib$^{19}$]hPTH(1-34)NH$_2$; [Cha$^{7\,11}$, Aib$^{16}$]hPTH(1-34)NH$_2$; [Aib$^{17}$]hPTH(1-34)NH$_2$; [Cha$^6$]hPTH(1-34)NH$_2$;[Cha$^{7\,11\,15}$]hPTH(1-34)NH$_2$; [Cha$^{7\,11}$, Nle$^{8\,18}$, Aib$^{19}$, Tyr$^{34}$]hPTH(1-34)NH$_2$; [Cha$^{7\,11}$, Nle$^{8\,18}$, Aib$^{19}$, Lys$^{30}$, Tyr$^{34}$]hPTH(1-34)NH$_2$; [Cha$^{7\,11\,15}$]hPTH(1-34)NH$_2$; [Aib$^{17}$]hPTH(1-34)NH$_2$; [Cha$^{7\,11}$, Leu$^{27}$]hPTH(1-34) NH$_2$; [Cha$^{7\,11\,15}$, Leu$^{27}$]hPTH(1-34)NH$_2$; [Cha$^{7\,11\,27}$]hPTH(1-34)NH$_2$; [Cha$^{7\,11\,15\,27}$]hPTH(1-34)NH$_2$; [Trp$^{15}$]hPTH(1-34)NH$_2$; [Nal$^{15}$]hPTH(1-34)NH$_2$; [Trp$^{15}$, Cha$^{23}$]hPTH(1-34)NH$_2$; [Cha$^{15\,23}$]hPTH(1-34)NH$_2$; [Phe$^{7\,11}$]hPTH(1-34)NH$_2$; [Nal$^{7\,11}$]hPTH(1-34)NH$_2$; [Trp$^{7\,11}$]hPTH(1-34)NH$_2$; [Phe$^{7\,11\,15}$]hPTH(1-34) NH$_2$; [Nal$^{7\,11\,15}$]hPTH(1-34)NH$_2$; [Trp$^{7\,11\,15}$]hPTH(1-34)NH$_2$; and [Tyr$^{7\,11\,15}$]hPTH(1-34)NH$_2$.

The following are specific examples of peptides encompassed by one or more of formulas (III) to (V), hereinabove: [Cha$^{7\,11}$]hPTHrP(1-34)NH$_2$; [Cha$^{11}$]hPTHrP(1-34)NH$_2$; [Cha$^{11}$]hPTHrP(1-34)NH$_2$; [Aib$^{16}$, Tyr$^{34}$hPTHrP(1-34)NH$_2$; [Aib$^{19}$]hPTHrP(1-34)NH$_2$; [Aib$^{16\,19}$]hPTHrP(1-34)NH$_2$;[Cha$^{7\,11}$, Aib$^{19}$]hPTHrP(1-34)NH$_2$; [Cha$^{22}$, Leu$^{23\,28\,31}$, Glu$^{25\,29}$, Lys$^{26\,30}$]hPTHrP(1-34)NH$_2$; [Glu$^{22\,25}$, Leu$^{23\,28\,31}$, Lys$^{26\,27\,30}$]hPTHrP(1-34)NH$_2$; [Cha$^{22\,23}$, Glu$^{25\,29}$, Leu$^{28\,31}$, Lys$^{26\,30}$]hPTHrP(1-34)NH$_2$; [Glu$^{22\,25}$, Leu$^{23\,28\,31}$, Aib$^{29}$, Lys$^{26\,30}$]hPTHrP(1-34)NH$_2$; [Glu$^{22\,25\,29}$, Lys$^{23\,26\,30}$, Leu$^{26\,31}$]hPTHrP(1-34)NH$_2$; [Glu$^{22\,25\,29}$, Leu$^{23\,28\,31}$, Lys$^{26}$, Cha$^{30}$]hPTHrP(1-34)NH$_2$; [Glu$^{22\,25\,28}$, Leu$^{23\,28\,31}$, Lys$^{25\,Aib30}$]hPTHrP(1-34)NH$_2$; [Glu$^{22\,25\,29}$, Leu$^{23\,31}$, Lys$^{26\,28\,30}$]hPTHrP(1-34) NH$_2$; [Cha$^{22\,23\,24\,27\,28\,31}$, Glu$^{26\,29}$, Lys$^{26\,30}$]hPTHrP(1-34)NH$_2$; [Glu$^{22\,25\,29}$, Cha$^{23\,24\,28\,31}$, Lys$^{26\,27\,30}$]hPTHrP(1-34)NH$_2$; [Glu$^{22\,25\,29}$, Cha$^{23\,24\,27\,31}$, Lys$^{26\,28\,30}$]hPTHrP(1-34)NH$_2$; [Glu$^{22\,25\,29}$, Lys$^{23\,26\,30}$, Cha$^{24\,27\,28\,31}$]hPTHrP(1-34)NH$_2$; [Cha$^{22}$, Leu$^{23\,28\,31}$, Glu$^{25\,29}$, Lys$^{26\,27\,30}$] hPTHrP(1-34)NH$_2$; [Cha$^{22}$, Leu$^{23\,31}$, Glu$^{25\,29}$, Lys$^{26\,28\,30}$]hPTHrP(1-34)NH$_2$; [Cha$^{22}$, Lys$^{23\,26\,30}$, Glu$^{25\,29}$, Leu$^{25\,31}$]hPHrP(1-34)NH$_2$; [Cha$^{22}$, Leu$^{23\,28\,31}$, Glu$^{26}$, Lys$^{26\,30}$, Aib$^{29}$]hPTHrP(1-34)NH$_2$; [Cha$^{22}$, Leu$^{23\,28\,31}$, Glu$^{25\,29}$, Lys$^{26}$, Aib$^{30}$]hPTHrP(1-34)NH$_2$; [Glu$^{22\,25}$, Leu$^{23\,28\,31}$, Lys$^{25\,27\,30}$, Aib$^{29}$]hPTHrP(1-34)NH$_2$; [Glu$^{22\,25}$, Lys$^{23\,26\,30}$, Leu$^{28\,31}$, Aib$^{29}$] hPTHrP(1-34)NH$_2$; [Glu$^{22\,25}$, Leu$^{23\,31}$, Lys$^{26\,28\,30}$, Aib$^{29}$]hPTHrP(1-34)NH$_2$; [Cha$^{7\,11}$, Glu$^{22\,25\,29}$, Leu$^{23\,28\,31}$, Lys$^{26\,30}$]hPTHrP(1-34)NH$_2$; [Cha$^{7\,11\,22}$, Leu$^{23\,28\,31}$, Glu$^{25\,29}$, Lys$^{26\,30}$]hPTHrP(1-34)NH$_2$; [Cha$^{7\,11}$, Glu$^{22\,25\,29}$, Leu$^{23\,28\,31}$, Lys$^{26\,27\,30}$]hPTHrP(1-34)NH$_2$; [Cha$^{7\,11\,22\,23}$, Glu$^{25\,29}$, Leu$^{28\,31}$, Lys$^{26\,30}$]hPTHrP(1-34)NH$_2$; [Cha$^{7\,11}$, Glu$^{22\,25\,29}$, Lys$^{23\,26\,30}$, Leu$^{28\,31}$]hPTHrP(1-34)NH$_2$; [Cha$^{7\,11}$, Glu$^{22\,25\,29}$, Leu$^{23\,31}$, Lys$^{26\,28\,30}$] hPTHrP(1-34)NH$_2$; [Cha$^{7\,11}$, Glu$^{22\,25}$, Leu$^{23\,28\,31}$, Aib$^{29}$, Lys$^{26\,30}$]hPTHrP(1-34)NH$_2$; [Cha$^{7\,11}$, Glu$^{22\,25\,29}$, Leu$^{23\,28\,31}$, Lys$^{26}$, Aib$^{30}$]hPTHrP(1-34)NH$_2$; [Cha$^{15}$, Glu$^{22\,25\,29}$, Leu$^{23\,28\,31}$, Lys$^{26\,30}$]hPTHrP(1-34) NH$_2$; [Cha$^{15\,22}$, Leu$^{23\,28\,31}$, Glu$^{25\,29}$, Lys$^{26\,30}$]hPTHrP(1-34)NH$_2$; [Cha$^{15}$, Glu$^{22\,25\,29}$, Leu$^{23\,28\,31}$, Lys$^{26\,27\,30}$]hPTHrP(1-34)NH$_2$;[Cha$^{15\,22\,23}$, Glu$^{25\,29}$, Leu$^{28\,31}$, Lys$^{26\,30}$]hPTHrP(1-34)NH$_2$; [Cha$^{15}$, Glu$^{22\,25}$, Leu$^{23\,28\,31}$, Aib$^{29}$, Lys$^{26\,30}$]hPTHrP(1-34)NH$_2$;[Cha$^{15}$, Glu$^{22\,25\,29}$, Lys$^{23\,25\,30}$, Leu$^{28\,31}$]hPTHrP(1-34) NH$_2$; [Cha$^{15}$, Glu$^{22\,25\,29}$, Leu$^{23\,28\,31}$, Lys$^{25}$, Aib$^{30}$]hPTHrP(1-34)NH$_2$; [Cha$^{15}$, Glu$^{22\,28\,29}$, Leu$^{23\,31}$, Lys$^{26\,28\,30}$] hPTHrP(1-34)NH$_2$; [Cha$^{15\,30}$, Glu$^{22\,25\,29}$, Leu$^{23\,28\,31}$, Lys$^{26}$]hPTHrP(1-34)NH$_2$;[Cha$^{7\,8\,22}$, Leu$^{23\,28\,31}$, Glu$^{25\,29}$, Lys$^{26\,30}$] hPTHrP(1-34)NH$_2$; [Cha$^{7\,8}$, Glu$^{22\,25\,29}$, Leu$^{23\,28\,31}$, Lys$^{26\,27\,30}$]hPTHrP(1-34)NH$_2$; [Cha$^{7\,8\,22\,23}$, Glu$^{25\,29}$, Leu$^{28\,31}$, Lys$^{26\,30}$] hPTHrP (1-34)NH$_2$; [Cha$^{7\,8}$, Glu$^{22\,25\,29}$, Leu$^{23\,28\,31}$, Lys$^{26\,30}$] hPTHrP(1-34)NH$_2$; [Cha$^{7\,8}$, Glu$^{22\,25}$, Leu$^{23\,28\,31}$, Aib$^{29}$, Lys$^{26\,30}$]hPTHrP(1-34) NH$_2$; [Cha$^{7\,8}$, Glu$^{22\,25\,29}$, Lys$^{23\,26\,30}$, Leu$^{28\,31}$]hPTHrP(1-34)NH$_2$;[Cha$^{7\,8}$, Glu$^{22\,25\,29}$, Leu$^{23\,28\,31}$, Lys$^{26}$, Aib$^{30}$] hPTHrP(1-34)NH$_2$; [Cha$^{7\,8}$, Glu$^{22\,25\,29}$, Leu$^{23\,31}$, Lys$^{26\,28\,30}$]hPTHrP(1-34)NH$_2$; [Cha$^{7\,8\,30}$, Glu$^{22\,25\,29}$, Leu$^{23\,28\,31}$, Lys$^{26}$]hPTHrP(1-34)NH$_2$; [Ser$^1$, Ile$^5$, Cha$^{7\,11\,22}$, Met$^8$, Asn$^{10}$, His$^{14}$, Leu$^{23\,28\,31}$, Glu$^{25\,25}$, Lys$^{26\,30}$]hPTHrP(1-34) NH$_2$; [Ser$^1$, Ile$^5$, Cha$^{7\,11}$, Met$^8$, Asn$^{10}$, His$^{14}$, Glu$^{22\,25\,29}$, Leu$^{23\,28\,31}$, Lys$^{26\,27\,30}$]hPTHrP(1-34)NH$_2$; [Ser$^1$, Ile$^5$, Cha$^{7\,11}$, Met$^8$, Asn$^{10}$, His$^{14}$, Glu$^{22\,25\,29}$, Leu$^{23\,31}$, Lys$^{26\,28\,30}$]hPTHrP(1-34) NH$_2$; Ser$^1$, Ile$^5$, Cha$^{7\,11}$, Met$^8$, Asn$^{10}$, His$^{14}$, Glu$^{22\,25\,29}$, Lys$^{23\,26\,30}$, Leu$^{28\,31}$]hPTHrP(1-34)NH$_2$; [Ser$^1$, Ile$^5$, Cha$^{7\,11}$, Met$^8$, Asn$^{10}$, His$^{14}$, Glu$^{22\,25}$, Leu$^{23\,28\,31}$, Aib$^{29}$, Lys$^{26\,30}$]hPTHrP(1-34) NH$_2$; [Ser$^1$, Ile$^5$, Cha$^{7\,11}$, Met$^8$, Asn$^{10}$, His$^{14}$, Glu$^{22\,25\,29}$, Leu$^{23\,28\,31}$, Lys$^{26}$, Aib$^{30}$] PTHrP(1-34)NH$_2$; [Ser$^1$, Ile$^5$, Cha$^{7\,11\,22\,23}$, Met$^8$, Asn$^{10}$, His$^{14}$, Glu$^{25\,29}$, Leu$^{28\,31}$, Lys$^{26\,30}$]hPTHrP(1-34) NH$_2$; [Ser$^1$, Ile$^5$, Cha$^{7\,11\,15}$, Met$^8$, Asn$^{10}$, His$^{14}$]hPTHrP(1-34)NH$_2$; [Ser$^1$, Ile$^5$, Met$^8$, Asn$^{10}$, Leu$^{11}$, His$^{14}$, Aib$^{18}$]hPTHrP (1-34)NH$_2$; [Ser$^1$, Ile$^5$, Met$^8$, Asn$^{10}$, Leu$^{11\,28\,31}$, His$^{14}$, Cha$^{22\,23}$, Glu$^{25\,29}$, Lys$^{26\,30}$]hPTHrP (1-34)NH$_2$; [Ser$^1$, Ile$^5$, Cha$^{7\,11}$, Met$^8$, Asn$^{10}$, His$^{14}$, Glu$^{22\,25\,29}$, Leu$^{23\,28\,31}$, Lys$^{26\,30}$]hPTHrP (1-34) NH$_2$; [Ser$^1$, Ile$^5$, Met$^8$, Asn$^{10}$, His$^{14}$, Cha$^{15}$, Glu$^{22\,25\,29}$, Leu$^{23\,28\,31}$, Lys$^{26\,30}$]hPTHrP (1-34)NH$_2$; [Ser$^1$, Ile$^5$, Cha$^{7\,8}$, Asn$^{10}$, His$^{14}$, Glu$^{22\,25\,29}$, Leu$^{23\,28\,31}$, Lys$^{25\,31}$, Lys$^{26\,30}$]hPTHrP(1-34)NH$^2$; [Glu$^{22\,25\,29}$, Leu$^{23\,28\,31}$, Lys$^{24\,26\,30}$]hPTHrP(1-34)NH$_2$; [Aib$^{22}$, Leu$^{23\,28\,31}$, Glu$^{25\,29}$, Lys$^{26\,30}$]hPTHrP(1-34)NH$_2$; [Glu$^{22\,29}$, Leu$^{23\,28\,31}$, Aib$^{25}$, Lys$^{26\,30}$]hPTHrP(1-34)NH$_2$; [Glu$^{22\,25\,29}$, Leu$^{23\,28\,31}$, Aib$^{26}$, Lys$^{30}$]hPTHrP (1-34)NH$_2$;

[Glu²² ²⁵ ²⁹, Leu²³ ²⁸, Lys²⁶ ³⁰ ³¹] hPTHrP(1-34)NH₂; [Ser¹, Ile⁵, Met⁸, Asn¹⁰, Leu¹¹ ²³ ²⁸ ³¹, His¹⁴, Cha²², Glu²⁵ ²⁹, Lys²⁸ ³⁰] hPTHrP(2-34)NH₂; [Ser¹, Ile⁵, Met⁸, Asn¹⁰, Leu¹¹ ²⁸ ³¹, His¹⁴, Glu²² ²⁵ ²⁹, Lys²³ ²⁶ ³⁰]PTHrP(1-34)NH₂; [Ser¹, Ile⁵, Met⁸, Asn¹⁰, Leu¹¹ ²³ ²⁸ ³¹, His¹⁴, Glu²² ²⁵ ²⁹, Lys²⁶ ²⁷ ³⁰] hPTHrP(1-34)NH₂; [Ser¹, Ile⁵, Met⁸, Asn¹⁰, Leu¹¹ ²³ ³¹, His¹⁴, Glu²² ²⁵ ²⁹, Lys²⁵ ²⁸ ³⁰] hPTHrP(1-34)NH₂; [Ser¹, Ile⁵, Met⁸, Asn¹⁰, Leu¹¹ ²³ ²⁸ ³¹, His¹⁴, Glu²² ²⁵, Aib²⁹, Lys²⁶ ³⁰] hPTHrP(1-34)NH₂; [Ser¹, Ile⁵, Met⁸, Asn¹⁰, Leu¹¹ ²³ ²⁸ ³¹, His¹⁴, Glu²² ²⁵ ²⁹, Lys²⁵, Aib³⁰] hPTHrP(1-34)NH₂; or [Ser¹, Ile⁵, Met⁸]hPTHrP(1-34)NH₂; [Glu²² ²⁵, Ahc²³, Lys²⁶ ³⁰, Leu²⁸ ³¹, Aib²⁹]hPTHrP(1-34)NH₂; [Glu²² ²⁶ Leu²³ ²⁸ ³¹, Lys²⁶ ³⁰, Ahc²⁷, Aib²⁹]hPTHrP(1-34)NH₂; [Glu²² ²⁵ Leu²³ ²⁸, Lys²⁶ ³⁰, Aib²⁹, Ahc³¹]hPTHrP(1-34)NH₂; [Glu²² ²⁵ Cha²³, Lys²⁶ ³⁰, Leu²⁸ ³¹, Aib²⁹]hPTHrP(1-34)NH₂; [Glu²² ²⁵ Cha²³, Lys²⁶ ³⁰, Leu²⁸, Aib²⁹]hPTHrP(1-34)NH₂; [Glu²² ²⁵ Cha²³, Lys²⁶ ³⁰, Aib²⁹]hPTHrP (1-34)NH₂; [Ahc²², Leu²³ ²⁸ ³¹, Glu²⁵, Lys²⁶ ³⁰, Aib²⁹]hPTHrP(1-34)NH₂; [Glu²² ²⁵, Leu²³ ²⁸ ³¹, Lys²⁶, Aib²⁹, Ahc³⁰]hPTHrP(1-34)NH₂; [Glu²² ²⁵, Cha²³, Lys²⁶ ³⁰, Aib²⁹, Leu³¹]hPTHrP(1-34)NH₂; [Glu²² ²⁵, Leu²³ ²⁸ ³¹, Ahc²⁴, Lys²⁶ ³⁰, Aib²⁹]hPTHrP(1-34)NH₂; [Glu²² ²⁵, Leu²³ ³¹, Lys²⁶ ³⁰, Ahc²⁸, Aib²⁹]hPTHrP(1-34)NH₂; [Glu²² ²⁵, Leu²³ ²⁸ ³¹, Lys²⁸, Aib²⁹ ³⁰] hPTHrP (1-34)NH₂; [Aib²² ²⁹, Leu²³ ²⁸ ³¹, Glu²⁵, Lys²⁶ ³⁰]hPTHrP(1-34) NH₂; [Glu²² ²⁵, Leu²³ ²⁸ ³¹, Aib²⁸ ²⁹, Lys³⁰]hPTHrP(1-34)NH₂; [Cha²², Ahc²³, Glu²⁵ ²⁹, Lys²⁶ ³⁰, Leu²⁸ ³¹]hPTHrP(1-34)NH₂; [Cha²², Leu²³ ²⁸ ³¹, Ahc²⁴, Glu²⁵ ²⁹, Lys²⁶ ³⁰]hPTHrP(1-34)NH₂; [Cha²², Leu²³ ²⁸ ³¹, Glu²⁵ ²⁹, Lys²⁶ ³⁰, Ahc²⁷]hPTHrP(1-34)NH₂; [Cha²², Leu²³ ³¹, Glu²⁵ ²⁹, Lys²⁶ ³⁰, Ahc²⁸]hPTHrP(1-34)NH₂; [Cha²², Leu²³ ²⁸ ³¹, Glu²⁵ ²⁹, Lys²⁶, Leu²⁸, Ahc³⁰]hPTHrP(1-34)NH₂; [Cha²² ²³, Glu²⁵ ²⁹, Lys²⁶ ³⁰, Leu³¹]hPTHrP (1-34)NH₂; [Cha²², Leu²³ ²⁸, Glu²⁵ ²⁹, Lys²⁶ ³⁰, Ahc³¹]hPTHrP(1-34)NH₂; [Cha²² ²³, Glu²⁵ ²⁹, Lys²⁶ ³⁰, Leu³¹]hPTHrP(1-34)NH₂; [Cha²² ²³, Glu²⁵ ²⁹, Lys²⁶ ³⁰, Leu²⁸]hPTHrP(1-34)NH₂; [Cha²² ²³, Glu²⁵ ²⁹, Lys²⁶ ³⁰] hPTHrP(1-34)NH₂; [Glu²², Leu²³ ²⁸ ³¹, Aib²⁵ ²⁹, Lys²⁶ ³⁰]hPTHrP(1-34) NH₂; [Glu²² ²⁹, Ahc²³, Aib²⁵, Lys²⁶ ³⁰, Leu²⁸ ³⁰, Leu²⁸ ³¹]hPTHrP(1-34) NH₂; [Ahc²², Leu²³ ²⁸ ³¹, Aib²⁵, Lys²⁶ ³⁰, Glu²⁹] hPTHrP(1-34)NH₂; [Aib²² ²⁵, Leu²³ ²⁸ ³¹, Lys²⁶ ³⁰, Glu²⁹]hPTHrP(1-34)NH₂; [Glu²² ²⁹, Leu²³ ²⁸ ³¹, Ahc²⁴, Aib²⁵, Lys²⁶ ³⁰]hPTHrP(1-34)NH₂; [Glu²² ²⁹, Leu²³ ²⁸ ³¹, Aib²⁵ ²⁶, Lys³⁰]hPTHrP(1-34)NH₂; [Glu²² ²⁹, Leu²³ ²⁸ ³¹, Aib²⁵, Lys²⁵ ³⁰, Ahc²⁷] hPTHrP(1-34)NH₂; [Glu²² ²⁹, Leu²³ ³¹, Aib²⁵, Lys²⁵ ³⁰, Ahc²⁸]hPTHrP(1-34)NH₂; [Glu²² ²⁹, Leu²³ ²⁹, Leu²³ ²⁸, Aib²⁵, Lys²⁶ ³⁰, Ahc³¹]hPTHrP(1-34)NH₂; [Glu²² ²⁹, Leu²³ ²⁸ ³¹, Aib²⁵ ³⁰, Lys²⁶] hPTHrP(1-34)NH₂; [Glu²² ²⁹, Leu²³ ²⁸ ³¹, Aib²⁵, Lys²⁶, Ahc³⁰]hPTHrP(1-34)NH₂; [Glu²² ²⁹, Cha²³, Aib²⁵, Lys²⁶ ³⁰, Leu²⁸ ³¹]hPTHrP(1-34)NH₂; [Glu²² ²⁹, Cha²³, Aib²⁵, Lys²⁶ ³⁰, Leu³¹]hPTHrP(1-34)NH₂; [Glu²² ²⁹, Cha²³, Aib²⁵, Lys²⁶ ³⁰] hPTHrP(1-34)NH₂; [Glu²² ²⁵ ²⁹, Cha²³, Aib²⁵, Lys²⁶ ³⁰, Leu²⁸]hPTHrP(1-34) NH₂; [Glu²² ²⁵ ²⁹, Cha²³, Lys²⁶, Leu²⁸ ³¹, Aib³⁰]hPTHrP (1-34)NH₂; [Glu²² ²⁵ ²⁹, Cha²³, Lys²⁶, Aib³⁰, Leu³¹]hPTHrP(1-34)NH₂; [Glu²² ²⁵ ²⁹, Cha²³, Lys²⁶, Aib³⁰]hPTHrP(1-34)NH₂; [Glu²² ²⁵ ²⁹, Cha²³, Lys²⁶, Leu²⁸, Aib³⁰]hPTHrP(1-34)Nh₂; [Glu²² ²⁵ ²⁹, Leu²³ ²⁸ ³¹, Lys²⁵, Ahc²⁷, Aib³⁰] hPTHrP(1-34) NH₂; [Glu²² ²⁵ ²⁹, Leu²³ ²⁸ ³¹, Ahc²⁴, Lys²⁶, Aib³⁰]hPTHrP (1-34)NH₂; [Ahc²², Leu²³ ²⁸ ³¹, Glu²⁵ ²⁹, Lys²⁶, Aib³⁰]hPTHrP(1-34)NH₂; [Aib²² ³⁰, Leu²³ ²⁸ ³¹, Glu²⁵ ²⁹, Lys²⁶]hPTHrP(1-34)NH₂; [Gky²² ²⁸, Lys²⁶ ³⁰ ³¹, Aib²⁹]hPTHrP(1-34) NH₂; [Cha²², Leu²³ ²⁸, Glu²⁵ ²⁹, Lys²⁶ ³⁰ ³¹]hPTHrP(1-34)NH₂; [Ahc²², Leu²³ ²⁸, Glu²⁵ ²⁹, Lys²⁵ ³⁰ ³¹] hPTHrP(1-34)NH₂; [Glu²² ²⁵ ²⁹, Leu²³ ²⁸, Lys²⁶ ³⁰ ³¹, Ahc³⁰]hPTHrP(1-34)NH₂; [Glu²² ²⁵ ²⁹, Leu²³ ²⁸ ³¹, Lys²⁶, Ahc³⁰]hPTHrP(1-34)NH₂; [Ahc²², Leu²³ ²⁸ ³¹, Glu²⁵ ²⁹, Lys²⁶ ³⁰]hPTHrP(1-34)NH₂; [Glu²² ²⁵ ²⁹, Leu²³ ²⁸, Lys²⁶ ³⁰ ³¹, Ahc²⁷]hPTHrP(1-34)NH₂.

In another aspect, the present invention is directed to a method of treating osteoporosis in a patient in need thereof, which comprises administering to said patient a compound of formula (I), (II), (III), (IV) or (V) or a pharmaceutically acceptable salt thereof, as defined hereinabove.

In another aspect, the present invention is directed to a method of treating osteoporosis in a patient in need thereof, which comprises administering to said patient a combination of a bisphosphonate or calcitonin and a compound of formula (I), (II), (III), (IV) or (V) or a pharmaceutically acceptable salt thereof, as defined hereinabove.

In another aspect, the present invention is directed to a pharmaceutical composition comprising a compound of formula (I), (II), (III), (IV) or (V) or a pharmaceutically acceptable salt thereof and a pharmaceutically acceptable carrier or diluent.

In another aspect, the present invention is directed to a pharmaceutical composition comprising a compound of formula (I), (II), (III), (IV) or (V) or a pharmaceutically acceptable salt thereof as defined hereinabove, a bisphosphonate or calcitonin and a pharmaceutically acceptable carrier or diluent.

In another aspect, the present invention is directed to a method of treating osteoporosis in a patient in need thereof, which comprises administering to said patient a peptide of the formula [Glu²² ²⁵, Leu²³ ²⁸ ³¹, Aib²⁹, Lys²⁶ ³⁰]hPTHrP(1-34) NH₂ or a pharmaceutically acceptable salt thereof.

In another aspect, the present invention is directed to a method of treating osteoporosis in a patient in need thereof, which comprises administering to said patient a combination of a bisphosphonate or calcitonin and a peptide of the formula [Glu²² ²⁵, Leu²³ ²⁸ ³¹, Aib²⁹, Lys²⁸ ³⁰]hPTHrP(1-34)NH₂ or a pharmaceutically acceptable salt thereof.

In another aspect, the present invention is directed to a pharmaceutical composition comprising a peptide of the formula [Glu²² ²⁵, Leu²³ ²⁸ ³¹, Aib²⁹, Lys²⁶ ³⁰]hPTHrP(1-34) NH₂ or a pharmaceutically acceptable salt thereof and a pharmaceutically acceptable carrier or diluent.

In another aspect, the present invention is directed to a pharmaceutical composition comprising a peptide of the formula [Glu²² ²⁵, Leu²³ ²⁸ ³¹, Aib²⁹, Lys²⁶ ³⁰]hPTHrP(1-34 (NH₂ or a pharmaceutically acceptable salt thereof, a bisphosphonate or calcitonin, and a pharmaceutically acceptable carrier or diluent.

In another aspect, the present invention is directed to a method of treating osteoporosis in a patient in need thereof, which comprises administering to said patient a peptide of the formula (VI):

(SEQ ID NO:5)

wherein
A₁ is Ala, Ser, or Dap;
A₃ is Ser or Aib;

$A_5$ is His, Ile, Acc, or Cha;
$A_7$ is Leu, Cha, Nle, β-Nal, Trp, Pal, Acc, Phe, or p-X-Phe in which X is OH, a halogen, or $CH_3$;
$A_8$ is Leu, Met, Acc, or Cha;
$A_{10}$ is Asp or Asn;
$A_{11}$ is Lys, Leu, Cha, Acc, Phe, or β-Nal;
$A_{12}$ is Gly, Acc, or Aib;
$A_{14}$ is Ser or His;
$A_{15}$ is Ile, Acc, or Cha;
$A_{16}$ is Gln or Aib;
$A_{17}$ is Asp or Aib;
$A_{18}$ is Leu, Aib, Acc, or Cha;
$A_{19}$ is Arg or Aib;
$A_{22}$ is Phe, Glu, Aib, Acc, or Cha;
$A_{23}$ is Phe, Leu, Lys, Acc, or Cha;
$A_{24}$ is Leu, Lys, Acc, or Cha;
$A_{25}$ is His, Lys, Aib, Acc, or Glu;
$A_{26}$ is His, Aib, Acc, or Lys;
$A_{27}$ is Leu, Lys, Acc, or Cha;
$a_{28}$ is Ile, Leu, Lys, Acc, or Cha;
$A_{29}$ is Ala, Glu, Acc, or Aib;
$A_{30}$ is Glu, Leu, Nle, Cha, Aib, Acc, or Lys;
$A_{31}$ is Ile, Leu, Cha, Lys, Acc, or deleted;
$A_{32}$ is His or deleted;
$A_{33}$ is Thr or deleted;
$A_{34}$ is Ala or deleted;
each of $R_1$ and $R_2$ is, independently, H, $C_{1-12}$ alkanyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; and
$R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$ or $CONH_2$;
provided that at least one of $A_5$, $A_7$, $A_8$, $A_{11}$, $A_{12}$, $A_{15}$, $A_{18}$, $A_{22}$, $A_{23}$, $A_{24}$, $A_{25}$, $A_{26}$, $A_{27}$, $A_{28}$, $A_{29}$, $A_{30}$, or $A_{31}$ is Acc; or a pharmaceutically acceptable salt thereof.

In another aspect, the present invention is directed to a method of treating osteoporosis in a patient in need thereof, which comprises administering to said patient a combination of a bisphosphonate or calcitonin and a peptide of formula (VI), as defined hereinabove.

In another aspect, the present invention is directed to a pharmaceutical composition comprising a pharmaceutically acceptable carrier or diluent and a peptide of formula (VI), as defined hereinabove.

In another aspect, the present invention is directed to a pharmaceutical composition comprising a bisphosphonate or calcitonin, a pharmaceutically acceptable carrier or diluent, and a peptide of formula (VI), as defined hereinabove.

With the exception of the N-terminal amino acid, all abbreviations (e.g. Ala or $A_1$) of amino acids in this disclosure stand for the structure of —NH—CH(R)—CO—, wherein R is a side chain of an amino acid (e.g. $CH_3$ for Ala). For the N-terminal amino acid, the abbreviation stands for the structure of =N—CH(R)—CO—, wherein R is a side chain of an amino acid. β-Nal, Nle, Dap, Cha, Nva, Amp, Pal, Ahc, and Aib are the abbreviations of the following α-amino acids; β-(2-naphthyl)alanine, norleucine, α,β-diaminopropionic acid, cyclohexylalanine, norvaline, 4-amino-phenylalanine, β-(3-pyridinyl)alanine. 1-amino-1-cyclo-hexanecarboxylic acid, and α-aminoisubutyric acid, respectively. What is meant by Acc is an amino acid selected from the group of 1-amino-1-cyclopropanecarboxylic acid:
1-amino-1-cyclobutanecarboxylic acid;
1-amino-1-cyclopentanecarboxylic acid;
1-amino-1-cyclohexanecarboxylic acid;
1-amino-1-cycloheptanecarboxylic acid;
1-amino-1-cyclooctanecarboxylic acid;
1-amino-1cyclononanecarboxylic acid. In the above formula, hydroxyalkyl, hydroxyphenyl-alkyl, and hydroxynaphthylalkyl may contain 1-4 hydroxy substituents. Also, $COE_1$ stands for —C=$O.E_1$. Examples of —C=$O.E_1$ include, but are not limited to, acetyl and phenylpropionyl.

A peptide of this invention is also denoted herein by another format, e.g, [Ahc$^{7\ 11}$]hPTH(1-34)$NH_2$, with the substituted amino acids from the natural sequence placed between the second set of brackets (e.g., Ahc$^7$ for Leu$^7$, and Ahc$^{11}$ for Leu$^{11}$ in hPTH). The abbreviation hPTH stands for human PTH, hPTHrP for human PTHrP, rPTH for rat PTH, and bPTH for bovine PTH. The numbers between the parentheses refer to the number of amino acids present in the peptide (e.g., hPTH(1-34) is amino acids 1 through 34 of the peptide sequence for human PTH). The sequences for hPTH (1-34), hPTHrP(1-34), bPTH(1-34), and rPTH(1-34) are listed in Nissenson, et al., Receptor, 3:193 (1993). The designation "$NH_2$" in PTH(1-34)$NH_2$ indicates that the C-terminus of the peptide is amidated. PTH(1-34), on the other hand, has a free acid C-terminus.

Each of the peptides of the invention is capable of stimulating the growth of bone in a subject (i.e., a mammal such as a human patient). Thus, it is useful in the treatment of osteoporosis and bone fractures when administered alone or concurrently with antiresorptive therapy, e.g., bisphosphonates and calcitonin.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject. The pill, tablet, or capsule that is to be administered orally can be coated with a substance for protecting the active composition from the gastric acid or testinal enzymes in the stomach for a period of time sufficient to allow it to pass undigested into the small intestine. The therapeutic composition can also be in the form of a biodegradable or nonbiodegradable sustained release formulation for subcutaneous or intramuscular administration. See, e.g., U.S. Pat. Nos. 3,773, 919 and 4,767,628 and PCT Application No. WO 94/15587. Continuous administration can also be achieved using an implantable or external pump (e.g., INFUSAID™ pump). The administration can also be conducted intermittently, e.g., single daily injection, or continuously at a low dose, e.g., sustained release formulation.

The dose of a peptide of the present invention for treating the above-mentioned diseases or disorders varies depending upon the manner of administration, the age and the body weight of the subject, and the condition of the subject to be treated, and ultimately will be decided by the attending physician or veterinarian.

Also contemplated within the scope of this invention is a peptide covered by the above generic formula for use in treating diseases or disorders associated with deficiency in bone growth or the like, e.g., osteoporosis or fractures.

Other features and advantages of the present invention will be apparent from the detailed description and from the claims.

DETAILED DESCRIPTION OF THE INVENTION

Based on the description herein, the present invention can be utilized to its fullest extent. The following specific examples are to be construed as merely illustrative, and should not be construed as a limitation of the remainder of the disclosure in any way whatsoever. Further, all publications cited herein are incorporated by reference.

Structure

PTH(1-34) and PTHrP(1-34) have been reported to have two amphophilic alpha helical domains. See, e.g., Barden, et al., Biochem., 32:7126 (1992). The first "-helix is formed between amino acid residues 4 through 13, while the second "-helix is formed between amino acid residues 21 through 29. Some peptides of this invention contain the substitution of Acc for one or more residues within or near these two regions of PTH(1-34) and PTHrP(1-34), e.g., $Ahc^7$ and $Ahc^{11}$ within the first "-helix or $Ahc^{27}$ and $Ahc^{28}$ within the second "-helix; or $Cha^7$ and $Cha^{11}$ within the first α-helix or $Cha^{27}$ and $Cha^{28}$ within the second α-helix.

Synthesis

The peptides of the invention can be prepared by standard solid phase synthesis. See, e.g., Stewart, J. M., et al., Solid Phase Synthesis (Pierce Chemical Co., 2d ed. 1984) The following is a description of how $[Glu^{22\ 25}, Leu^{23\ 28}, Lys^{26\ 30}, Aib^{29}, Ahc^{31}]hPTH(1-34)NH_2$ was prepared. Other peptides of the invention can be prepared in an analogous manner by a person of ordinary skill in the art.

1-[N-tert-Butoxycarbonyl-amino]-1-cyclohexane-carboxylic acid (Boc-Ahc-OH) was synthesized as follows:

19.1 g (0.133 mol) of 1amino-1cyclohexanecarboxylic acid (Acros Organics, Fisher Scientific, Pittsburgh, Pa.) was dissolved in 200 ml of dioxane and 100 ml of water. To it was added 67 mg of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). Two organic layers were combined and washed with water (2×150 ml), dried over anhydrous $MgSO_4$, filtered, and concentrated to dryness under reduced pressure. The residue was recrystallized in ethyl acetate/hexanes. 9.2 g of a pure product was obtained. 29% yield. Other protected Acc amino acids can be prepared in an analogous manner by a person or ordinary skill in the art.

The peptide was synthesized on an Applied Biosystems (Foster City, Calif.) model 430A peptide synthesizer which was modified to do accelerated Boc-chemistry solid phase peptide synthesis. See Schnoize, et al., Int. J. Peptide Protein Res., 90:180 (1992). 4-Methylbenz-hydrylamine (MBHA) resin (Peninsula, Belmont, Calif.) with the substitution of 0.93 mmol/g was used. The Boc amino acis (Bachem, Calif., Torrance, Calif.; Nova Biochem., LaJolla, Calif.) were used with the following side chain protection. Boc-Ala-OH, Boc-Arg(Tos)-OH, Boc-Asp(OcHex)-OH, Boc-Glu(OcHex)-OH, Boc-His(DNP)-OH, Boc-Val-OH, Boc-Leu-OH, Boc-Gly-OH, Boc-Gln-OH, Boc-Ile-OH, Boc-Lys(2ClZ)-OH, Boc-Ahc-OH, Boc-Thr(Bzl)-OH, Boc-Ser(Bzl)-OH; and Boc-Aib-OH. The synthesis was carried out on a 0.14 mmol scale. The Boc groups were removed by treatment with 100% TFA for 2×1 min. Boc amino acids (2.5 mmol) were pre-activated with HBTU (2.0 mmol) and DIEA (1.0 mL) in 4 1mL of DMF and were coupled without prior neutralization of the peptide-resin TFA salt. Coupling times were 5 min except for the Boc-Aib-OH, and its following residue Boc-Leu-OH, and Boc-Ahc-OH, and its following residue Boc-Lys(2 Clz)-OH, wherein the coupling times for these four residues were 2 hrs.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. The partially-deproteted peptide-resin was washed with DMF and DCM and dried under reduced pressure. The final cleavage was done by stirring the peptide-resin in 10 mL of HF containing 1 mL of anisole and dithiothreitol (24 mg) at OEC for 75 min. HF was removed by a flow of nitrogen. The residue was washed with ether (6×10 mL) and extracted with 4N HOAc (6×10 mL).

The peptide mixture in the aqueous extract was purified on a reversed-phase preparative high pressure liquid chromatography (HPLC) using a reversed phase VYDAC™ $C_{18}$ column (Nest Group, Southborough, Mass.). The column was eluted with a linear gradient (10% to 45% of solution B over 130 min.) at a flow rate of 10 mL/min (Solution A=0.1% aqueous TFA. Solution B=acetonitrile containing 0.1% of TFA). Fractions were collected and checked on analytical HPLC. Those containing pure product were combined and lyophilized to dryness. 85 mg of a white solid was obtained. Purity was >99% based on analytical HPLC analysis. Electro-spray mass spectrometer analysis gave the molecular weight at 3972.4 (in agreement with the calculated molecular weight of 3972.7).

The synthesis and purification of $[Cha^{22}, Leu^{23\ 28\ 31}, Glu^{25}, Lys^{26\ 30}, Ahc^{27}, Aib^{29}]hPTHrP(1-34)NH_2$ was carried out in the same manner as the above synthesis of $[Glu^{22\ 25}, Leu^{28}, Lys^{26\ 30}, Aib^{29}, Ahc^{31}]hPTHrP(1-34)NH_2$. The protected amino acid Boc-Cha-OH was purchased from, Bachem, Calif. The purity of the final product was >99%, and the electron-spray mass spectrometer gave the molecular weight at 3997.2 (calculated molecular weight is 3996.8).

The following is a description of how $[Aib^{34}]hPTH(1-34)NH_2$ was prepared. The peptide, $[Aib^{34}]hPTH(1-34)NH_2$, was synthesized on an Appiled Biosystems (Foster City, Calif.) model 430A peptide synthesizer which was modified to do accelerated Boc-chemistry solid phase peptide synthesis. See Schnoize, et al., Int. J. Peptide Protein Res,. 90:180 (1992). 4-Methylbenz-hydrylamine (MBHA) resin (Peninsula, Belmont, Calif.) with the substitution of 0.93 mmol/g was used. The Boc amino acids (Bachem, Calif., Torrance, Calif.; Nova Biochem., Lajolla, Calif.) were used with the following side chain protection: Boc-Arg(Tos)-OH, Boc-Asp (OcHxl)-OH, Boc-Asn(Xan)-OH, Boc-Glu(OcHxl)-OH, Boc-His(DNP)-OH, Boc-Asn-GH, Boc-Val-OH, Boc-Leu-OH, Boc-Ser-OH, Boc-Gly-OH, Boc-Met-OH, Boc-Gln-OH, Boc-Ile-OH. Boc-Lys(2ClZ)-OH, Boc-Ser(Bzl)-OH, and Boc-Trp(Fm)-OH. The synthesis was carried out on a 0.14 mmol scale. The Boc groups were removed by treatment with 100% TFA for 2×1 min. Box amino acids (2.5 mmol) were pre-activated with HBTU (2.1 mmol) and DIEA (1.0 mL) n 4 mL of DMF and were coupled without prior neutralization of the peptide-resin TFA salt. Coupling times were 5 min except for the Boc-Aib-OH and the following residue, Boc-Asn(Xan)-OH, wherein the coupling times were 20 min.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min.), the formyl group on the side chain of Trp was removed by treatment with a solution of 15% ethanolamine/15% water/

70% DMF for 2×30 min. The partially-deprotected peptide-resin was washed with DMF and DCM and dried under reduced pressure. The final cleavage was done by stirring the peptide-resin in 10 mL of HF containing 1 mL of anisole at 0° C. for 75 min. HF was removed by a flow of nitrogen. The residue was washed with ether (6×10 ) mL) and extracted with 4N HOAc (6×10 mL).

The peptide mixture in the aqueous extract was purified on a reversed-phase preparative high pressure liquid chromatography (HPLC) using a reversed phase VYDAC™ $C_{18}$ column (Nest Group, Southborough, Mass.). The column was eluted with a linear gradient (10% to 45% of solution B over 130 min.) at a flow rate of 10 mL/min (Solution A=0.1% aqueous TFA; Solution B=acetonitrile containing 0.1% of TFA). Fractions were collected and checked on analytic HPLC. Those containing pure product were combined and lyophilized to dryness. 62.3 mg of a white solid was obtained. Purity was >99% based on analytical HPLC analysis. Electro-spray mass spectrometer analysis gave the molecular weight at 4054.7 (in agreement with the calculated molecular weight of 4054.7).

The synthesis and purification of [Cha$^{7\ 11}$]hPTH(1-34)NH$_2$ was carried out in the same manner as the above synthesis of [Aib$^{34}$]hPTH(1-34)NH$_2$. The protected amino acid Boc-Cha-OH was purchased from Bachem, Calif. The purity of the final product was >98%, and the electron-spray mass spectrometer gave the molecular weight at 4197.0 (calculated molecular weight is 4196.9).

The following is a description of how [Glu$^{22\ 25}$, Leu$^{23\ 28}$, Lys$^{26\ 30}$, Aib$^{29}$, Ahc$^{31}$]hPTH(1-34)NH$_2$ was prepared. Other peptides of the invention can be prepared in an analogous manner by a person of ordinary skill in the art.

1-[N-tert-Butoxycarbonyl-amino]-1-cyclohexane-carboxylic acid (Boc-Ahc-OH) was synthesized as follows.

19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 mg of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). Two organic layers were combined and washed with water (2×150 ml), dried over anhydrous MgSO$_4$, filtered, and concentrated to dryness under reduced pressure. The residue was recrystallized inn ethyl acetate/hexanes. 9.2 g of a pure product was obtained. 29% yield. Other protected Acc amino acids can be prepared in an analogous manner by a person or ordinary skill in the art.

The peptide was synthesized on an Applied Biosystems (Foster City, Calif.) model 430A peptide synthesizer which was modified to do accelerated Boc-chemistry solid phase peptide synthesis. See Schnoize, et al., Int. J. Peptide Protein Res., 90:180 (1992). 4-Methylbenz-hydrylamine (MBHA) resin (Peninsula, Belmont, Calif.) with the substitution of 0.93 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Glu(OcHex)-OH, Box-His(DNP)-OH, Boc-Val-OH, Boc-Leu-OH, Boc-Gly-OH, Boc-Gln-OH, Boc-Lys(2ClZ)-OH, Boc-Ahc-OH, Boc-Thr(Bzl)-OH, Box-Ser(Bzl)-OH; and Box-Aib-OH. The synthesis was carried out on a 0.14 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min except for the Boc-Aib-OH, and its following residue Boc-Leu-OH and Boc-Ahc-OH, and its following residue Boc-Lys(2Clz)-OH, wherein the coupling times for these four residues were 2 hours.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. The partially-deprotected peptide-resin was washed with DMF and DCM and dried under reduced pressure. The final cleavage was done by stirring the peptide-resin in 10 mL of HF containing 1 mL of anisole and dithiothreitol (24 mg) at 0° C. for 75 min. HF was removed by a flow of nitrogen. The residue was washed with ether (6×10 mL) and extracted with 4N HOAc (6×10 mL).

The peptide mixture in the aqueous extract was purified on a reversed-phase preparative high pressure liquid chromatography (HPLC) using a reversed phase VYDAC™ $C_{18}$ column (Nest Group, Southborough, Mass.). The column was eluted with a linear gradient (10% to 45% of solution B over 130 min.) at a flow rate of 10 mL/min (Solution A=0.1% aqueous TFA: Solution B=acetonitrile containing 0.1% of TFA). Fractions were collected and checked on analytical HPLC. Those containing pure product were combined and lyophilized to dryness. 85 mg of a white solid was obtained. Purity was >99% based on analytical HPLC analysis. Electro-spray mass spectrometer analysis gave the molecular weight at 3972.4 (in agreement with the calculated molecular weight of 3972.7).

The synthesis and purification of [Cha$^{22}$, Leu$^{23\ 28\ 31}$, Glu$^{25}$, Lys$^{26\ 30}$, Ahc$^{27}$, Aib$^{29}$]hPTHrP(1-34)NH$_2$ was carried out in the same manner as the above synthesis of [Glu$^{22\ 25}$, Leu$^{23\ 28}$, Lys$^{26\ 30}$, Aib$^{29}$, Ahc$^{31}$]hPTHrP(1-34)NH$_2$. The protected amino acid Boc-Cha-OH was purchased from Bachem, Calif. The purity of the final product was >99%, and the electron-spray mass spectrometer gave the molecular weight at 3997.2 (calculated molecular weight is 3996.8).

The full names for the abbreviations used above are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane. HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2ClZ for 2-chlorobenzyloxycarbonyl, and OcHex for O-cyclohexyl.

The substituents $R_1$ and $R_2$ of the above generic formula may be attached to the free amine of the N-terminal amino acid by standard methods known in the art. For example, alkyl groups, e.g., $C_{1-12}$ alkyl, may be attached using reductive alkylation. Hydroxyalkyl groups, e.g., $C_{1-12}$ hydroxyalkyl, may also be attached using reductive alkylation wherein the free hnydroxy group is protected with a t-butyl ester. Acyl groups, e.g., may be attached by coupling the free acid, e.g., $E_1COOH$, to the free amine of the N-terminal amino acid by mixing the completed resin with 3 molar equivalents of both the free acid and diisopropylcarbodiimide in methylene chloride for one hour and cycling the resulting resin through steps (a) to (f) in the above wash program. If the free acid contains a free hydroxy group, e.g., p-hydroxyphenylpropionic acid, then the coupling should be performed with an additional 3 molar equivalents of HOBT.

Other peptides of this invention can be prepared in an analogous manner by a person of ordinary skill in the art.

Functional Assays

A. Binding to PTH Receptor

The peptides of the invention were tested for their ability to bind to the PTH receptor present on SaOS-2 (human osteosarcoma cells). SaOS-2 cells (American Type Culture Collection, Rockville, Md.; ATCC #HTB 85) were maintained in RPMI 1640 medium (Sigma, St. Louis, Mo.) supplemented with 10% fetal bovine serum (FBS) and 2 mM glutamine at 3EC in a humidified atmosphere of 5% $CO_2$ in air. The medium was changed every three or four days, and the cells were subcultured every week by trypsinization.

SaOS-2 cells were maintained for four days until they had reached confluence. The medium was replaced with 5% FBS in RPMI 1640 medium and incubated for 2 hrs at room temperature with $10 \times 10^4$ cpm mono-$^{125}$I-[Nle$^{8\ 18}$, Tyr$^{34}$ (3-$^{125}$I)] bPTH(1-34)NH$_2$ in the presence of a competing peptides of the invention at various concentrations between $10^{-11}$ M to $10^{-4}$ M. The cells were washed four times with ice-cold PBS and lysed with 0.1 M NaOH, and the radioactivity associated with the cells was counted in a scintillation counter. Synthesis of mono-$^{125}$I-[Nle$^{8\ 18}$, Tyr$_{34}$(3-$^{125}$I)]bPTH (1-34)NH$_2$ was carried out as described in Goldman, M. E., el al., Endocrinol., 123:1468 (1988).

The binding assay was conducted with various peptides of the invention and the Kd value (half maximal inhibition of binding of mono-$^{125}$I-[Nle$^{8\ 18}$, Tyr$^{34}$(3-$^{125}$I)]bPTH(1-34) NH$_2$) for each peptide was calculated.

As shown in Table I, all of the tested peptides had a high binding affinity for the PTH receptor on the SaOS-2 cell.

B. Stimulation of Adenylate Cyclase Activity

The ability of the peptides of the invention to induce a biological response in SaOS-2 cells were measured. More specifically, any stimulation of the adenylate cyclase was determined by measuring the level of synthesis of cAMP (adenosine 3', 5'-monophosphate) as described previously in Rodan, et al., J. Clin. Invest. 72; 1511 (1983) and Goldman, et al., Endocrinol., 123:1468 (1988). Confluent SAOS-2 cells in 24 wells plates were incubated with 0.5.Cl [$^3$H]adenine (26.9 Cl/mmol, New England Nuclear, Boston, Mass.) in fresh medium at 37EC for 2 hrs, and washed twice with Hank's balanced salt solution (Gibco, Gaithersburg, Md.). The cells were treated with 1 mM IBMX [isobutylmethyl-xanthine, Sigma, St. Louis, Mo.] in fresh medium for 15 min, and the peptides of the invention were added to the medium to incubate for 5 min. The reaction was stopped by the addition of 1.2 M trichloroacetic acid (TCA) (Sigma, St. Louis, Mo.) followed by sample neutralizaton with 4N KOH. cAMP was isolated by the two-column chromatographic method (Salmon, et al., 1974, Anal. Biochem. 58, 541). The radioactivity was counted in a scintillation counter (Liquid Scintillation Counter 2200CA, PACKARD, Downers Grove, Ill.).

The respective $EC_{50}$ values (half maximal stimulation of adenylate cyclase) for the tested peptides were calculated and shown in Table I. All tested peptides were found to be potent stimulators of adenylate cyclase activity, which is a biochemical pathway indicative as a proximal signal for osteoblast proliferation (e.g., bone growth).

TABLE I

| PEPTIDE | Kd (μM) | $EC_{50}$ (nM) |
|---|---|---|
| [Cha$^{7,11}$]hPTH(1-34)NH$_2$ | 0.01 | 0.6 |
| [Cha$^{23}$]hPTH(1-34)NH$_2$ | 0.2 | 20 |
| [Cha$^{24}$]hPTH(1-34)NH$_2$ | 0.1 | 10 |
| [Nle$^{8,18}$, Cha$^{22}$]hPTH(1-34)NH$_2$; | 0.05 | 2 |
| [Cha$^{28}$]hPTH(1-34)NH$_2$ | 0.05 | 2.5 |
| [Cha$^{31}$]hPTH(1-34)NH$_2$ | 0.03 | 4 |
| [Aib$^{16}$]hPTH(1-34)NH$_2$; | 0.004 | 0.7 |
| [Aib$^{19}$]hPTH(1-34)NH$_2$; | 0.005 | 0.6 |
| [Aib$^{34}$]hPTH(1-34)NH$_2$; | 0.007 | 3 |
| [Nle$^{31}$]hPTH(1-34)NH$_2$; | 0.004 | 0.7 |
| [hArg$^{27}$]hPTH(1-34)NH$_2$ | 0.007 | 1 |
| [Dap, Nle$^{8,18}$, Tyr$^{34}$]hPTH(1-34)NH$_2$; | 0.150 | 10 |
| [Cha$^{24,28,31}$, Lys$^{30}$]hPTH(1-34)NH$_2$; | 0.5 | 7 |
| [Cha$^{7,11}$, Nle$^{8,18}$, Tyr$^{34}$]hPTH(1-34)NH$_2$ | 0.006 | 0.6 |
| [Cha$^{7,11}$, Nle$^{8,18}$, Aib$^{16,\ 19}$, Tyr$^{34}$]hPTH (1-34)NH$_2$ | 0.005 | 1.5 |
| [Cha$^{7,11}$, Nle$^{8,18,31}$, Aib$^{16,\ 19}$, Tyr$^{34}$]hPTH(1-34)NH$_2$ | 0.04 | 4 |
| [Cha$^{11}$]hPTH(1-34)NH$_2$ | 0.005 | 2 |
| [Cha$^{28,\ 31}$]hPTH(1-34)NH$_2$ | 0.06 | 7 |
| [Cha$^{7,11}$, Nle$^{8,18}$, Aib$^{34}$]hPTH(1-34)NH$_2$ | 0.03 | 1.5 |
| [Cha$^{18}$]hPTH(1-34)NH$_2$ | 0.005 | 1.3 |
| [Cha$^{7,11}$, Aib$^{19}$]hPTH(1-34)NH$_2$ | 0.007 | 0.5 |
| [Cha$^{7,11}$, Aib$^{16}$]hPTH(1-34)NH$_2$ | 0.004 | 1.1 |
| [Aib$^{15,\ 19}$]hPTH(1-34)NH$_2$ | 0.004 | 0.6 |
| [Aib$^{12}$]hPTH(1-34)NH$_2$ | 0.005 | 2 |
| [Aib$^{3}$]hPTH(1-34)NH$_2$ | 0.004 | 1.1 |
| [Cha$^{7,11}$, Aib$^{19}$, Lys$^{30}$]hPTH(1-34)NH$_2$ | 0.004 | 2 |
| [Cha$^{7}$]hPTH(1-34)NH$_2$ | 0.02 | 2.3 |
| [Cha$^{24,28,\ 31}$]hPTH(1-34)NH$_2$ | 1.0 | 30 |
| [Aib$^{17}$]hPTH(1-34) | 0.05 | 3 |
| [Cha$^{7,11,15}$]hPTH(1-34) | 0.01 | 1.4 |

TABLE II

| PEPTIDE | Kd (μM) | $EC_{50}$ (nM) |
|---|---|---|
| [Glu$^{22,25}$, Leu$^{23,28}$, Lys$^{26,30}$, Aib$^{29}$, Ahc$^{31}$]hPTHrP(1-34)NH$_2$ | 0.200 | 3.7 |
| [Glu$^{22,25}$, Ahc$^{23}$, Lys$^{26,30}$, Leu$^{28,31}$, Aib$^{29}$]hPTHrP(1-34)NH$_2$ | 0.070 | 3.9 |
| [Glu$^{22,25}$, Leu$^{23,28,31}$, Lys$^{26,30}$, Ahc$^{27}$, Aib$^{29}$]hPTHrP(1-34)NH$_2$ | 0.230 | 3.0 |
| [Glu$^{22,25,29}$, Leu$^{23,28,31}$, Lys$^{26}$, Ahc$^{30}$]hPTHrP(1-34)NH$_2$ | 0.230 | 20 |
| [Cha$^{22}$, Leu$^{23,28,31}$, Glu$^{25}$, Lys$^{26,30}$, Ahc$^{27}$, Aib$^{29}$]hPTHrP(1-34)NH$_2$ | 0.060 | 2.0 |
| [Glu$^{22,25}$, Leu$^{23,28,31}$, Ahc$^{24}$, Lys$^{26,30}$, Aib$^{29}$]hPTHrP(1-34)NH$_2$ | 0.006 | 0.5 |
| [Glu$^{22,29}$, Leu$^{23,28,31}$, Aib$^{25}$, Lys$^{26,30}$, Ahc$^{27}$]hPTHrP(1-34)NH$_2$ | | 5 |
| [Glu$^{22}$, Leu$^{23,28,31}$, Aib$^{25,29}$, Lys$^{26,30}$, Ahc$^{27}$]hPTHrP(1-34)NH$_2$ | | 2 |
| [Ahe$^{22}$, Leu$^{23,28,31}$, Glu$^{25}$, Lys$^{26,30}$, Aib$^{29}$]hPTHrP(1-34)NH$_2$ | | 0.3 |
| [Glu$^{22,25}$, Leu$^{23,31}$, Lys$^{26,30}$, Ahe$^{28}$, Aib$^{29}$]hPTHrP(1-34)NH$_2$ | | 0.5 |
| [Cha$^{22}$, Ahc$^{23}$, Glu$^{25}$, Lys$^{26,30}$, Leu$^{28,31}$, Aib$^{29}$]hPTHrP(1-34)NH$_2$ | | 0.4 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of treating osteoporosis in a patient in need thereof, which comprises administering to said patient a peptide of the formula:

(SEQ ID NO:6)

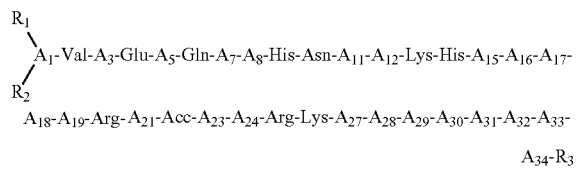

wherein
- $A_1$ is Ser, Ala or Dap;
- $A_3$ is Ser, Thr or Aib;
- $A_5$ is Leu, Nle, Ile, Cha, β-Nal, Trp, Pal, Acc, Phe or p-X-Phe in which X is OH, a halogen or $CH_3$;
- $A_7$ is Leu, Nle, Ile, Cha, β-Nal, Trp, Acc, Pal, Phe or p-X-Phe in which X is OH, a halogen or $CH_3$;
- $A_8$ is Met, Nva, Leu, Val, Ile, Cha, Acc or Nle;
- $A_{11}$ is Leu, Nle, Ile, Cha, β-Nal, Trp, Pal, Acc, Phe or p-X-Phe in which X is OH, a halogen, or $CH_3$;
- $A_{12}$ is Gly, Acc or Aib;
- $A_{15}$ is Leu, Nle, Ile, Cha, β-Nal, Trp, Pal, Acc, Phe or p-X-Phe in which X is OH, a halogen or $CH_3$;
- $A_{16}$ is Ser, Asn, Ala or Aib;
- $A_{17}$ is Ser, Thr or Aib;
- $A_{18}$ is Met, Nva, Leu, Val, Ile, Nle, Acc, Cha or Aib;
- $A_{19}$ is Glu or Aib;
- $A_{21}$ is Val, Acc, Cha or Met;
- $A_{23}$ is Trp, Acc or Cha;
- $A_{24}$ is Leu, Acc or Cha;
- $A_{27}$ is Lys, Aib, Leu, hArg, Gln, Acc or Cha;
- $A_{28}$ is Leu, Acc or Cha;
- $A_{29}$ is Gln, Acc or Aib;
- $A_{30}$ is Asp or Lys;
- $A_{31}$ is Val, Leu, Nle, Acc, Cha, or deleted;
- $A_{32}$ is His or deleted;
- $A_{33}$ is Asn or deleted;
- $A_{34}$ is Phe, Tyr, Amp, Aib, or deleted;
- each of $R_1$ and $R_2$ is, independently, H, $C_{1-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxyphenylalkyl or $C_{11-20}$ hydroxynaphthylalkyl; or one and only one of $R_1$ and $R_2$ is $COE_1$ in which $E_1$ is $C_{1-12}$ alkyl, $C_{2-12}$ alkenyl, $C_{7-20}$ phenylalkyl, $C_{11-20}$ naphthylalkyl, $C_{1-12}$ hydroxyalkyl, $C_{2-12}$ hydroxyalkenyl, $C_{7-20}$ hydroxy-phenylalkyl or $C_{11-20}$ hydroxynaphthylalkyl; and
- $R_3$ is OH, $NH_2$, $C_{1-12}$ alkoxy or NH—Y—$CH_2$—Z in which Y is a $C_{1-12}$ hydrocarbon moiety and Z is H, OH, $CO_2H$ or $CONH_2$;

provided that at least one of $A_5$, $A_7$, $A_8$, $A_{11}$, $A_{12}$, $A_{15}$, $A_{18}$, $A_{21}$, $A_{23}$, $A_{24}$, $A_{27}$, $A_{28}$, $A_{29}$ and $A_{31}$ is Acc; or a pharmaceutically acceptable salt thereof.

2. The method according to claim 1, further comprising administering to said patient a bisphosphonate or calcitonin.

* * * * *